United States Patent [19]
Spireas et al.

[11] Patent Number: 5,968,550
[45] Date of Patent: Oct. 19, 1999

[54] LIQUISOLID SYSTEMS AND METHODS OF PREPARING SAME

[76] Inventors: Spiridon Spireas, 177 Arlington Ave., 2nd Floor, Clifton, N.J. 07011; Sanford M. Bolton, 5495 N. Via Velazquez, Tuscon, Ariz. 85750

[21] Appl. No.: 08/937,240

[22] Filed: Oct. 1, 1997

Related U.S. Application Data

[62] Division of application No. 08/658,514, Jun. 10, 1996, Pat. No. 5,800,834.

[51] Int. Cl.$^6$ ........................................................ A61K 9/20
[52] U.S. Cl. .......................... 424/451; 424/456; 424/457; 424/458; 424/459; 424/461; 424/462; 424/464; 424/465; 424/468; 424/489; 424/490; 424/493; 424/494; 424/497; 424/501
[58] Field of Search ..................................... 424/451, 456, 424/457, 458, 459, 461, 462, 464, 465, 468, 489, 490, 493, 494, 497, 501

[56] References Cited

PUBLICATIONS

"Powdered Solution Technology: Principles and Mechanism", Pharm. Res. 9: 1351–1368, Apr. 1992.

"Use of Powdered Solutions to Improve the Dissolution Rate of Polythiazide Tablets", Drug. Dev. Ind. Pharm. 16: 769–777, May 1990.

*Primary Examiner*—Frederick Krass
*Attorney, Agent, or Firm*—Caesar, Rivise, Bernstein, Cohen & Pokotilow, Ltd.

[57] ABSTRACT

Liquisolid systems are acceptably flowing and compressible powdered forms of liquid medications. According to the concept of liquisolid systems, liquid lipophilic drugs, or water-insoluble solid drugs dissolved in suitable non-volatile solvents, may be converted into free-flowing and readily compressible powders by a simple admixture with selected powder excipients referred to as the carrier and coating materials. Various grades of microcrystalline or amorphous cellulose may be used as carriers, whereas very fine particle size silica powders may be used as coating materials. Based on the theory that the carrier and coating materials can retain only certain amounts of liquid and at the same time maintain acceptable flow and compression properties, a new formulation-mathematical model is provided to calculate the optimum quantities of carrier and coating materials required to yield acceptably flowing and compressible liquid/powder admixtures.

25 Claims, 9 Drawing Sheets

LIQUISOLID SYSTEMS AND METHODS OF PREPARING SAME

This is a division of application Ser. No. 08/658,514, filed Jun. 10, 1996, now U.S. Pat. No. 5,800,834.

FIELD OF THE INVENTION

The present invention relates to powdered forms of liquid medications formulated to have both acceptable flow and acceptable compression characteristics, and methods of producing them.

DESCRIPTION OF THE RELATED ART

It is well established that the active ingredient in a solid dosage form must undergo dissolution before it is available for absorption from the gastrointestinal tract. The rate of absorption of a sparingly water-soluble drug, formulated as an orally administered solid dosage form, is controlled by its dissolution rate in the fluid present at the absorption site, i.e., the dissolution rate is often the rate-determining step in drug absorption. Since they exhibit poor and erratic dissolution profiles, most water-insoluble drugs are included by the FDA in the list of drugs having a high risk for therapeutic inequivalence due to differences and inconsistencies in bioavailability.

Various techniques have been employed to formulate drug delivery systems which would enhance the dissolution profile and, in turn, the absorption efficiency of water-insoluble solid drugs such as digoxin, digitoxin, prednisolone, hydrocortisone, prednisone, spironolactone, hydrochlorothiazide, polythiazide, and/or liquid lipophilic medications such as clofibrate, chlorpheniramine, water-insoluble vitamins, fish oil, etc. Drug micronization, solid dispersion, coprecipitation, lyophilization, microencapsulation and inclusion of drug solutions or liquid drugs into soft gelatin capsules or specially sealed hard shell capsules are some of the major formulation tools which have been shown to enhance the dissolution characteristics of water-insoluble drugs.

Despite their high production cost and technologically demanding, patented and advanced preparations, soft gelatin capsules represent a unique approach for the formulation of liquid oily medications and/or drug solutions of water-insoluble solid drugs. Comparing various digoxin oral solid dosage forms, Ebert (1) has reported that soft gelatin capsule products demonstrated the highest and most consistent bioavailability, mainly due to the fact that the drug is already in solution. Nelson, in his review (2), points out that the availability of drug for absorption from various types of oral formulations, usually decreases in the following order: solution, suspension, powdered-filled capsule, compressed tablet, coated tablet.

A more recent technique, entitled "powdered solution technology", has been applied to prepare water-insoluble drugs into rapid release solid dosage forms. Powdered solutions are designed to contain liquid medications in powdered form, thereby possessing mechanisms of drug delivery similar to those of soft gelatin capsule preparations containing liquids. The concept of powdered solutions enables one to convert drug solutions or liquid drugs into acceptably flowing powders by a simple admixture with selected powder excipients (e.g., cellulose and silica). Several investigators (3–8) have used a similar approach to improve the release profiles of several water-insoluble drugs.

However, the industrial application of this technique has been hampered by the poor and erratic flowability and compressibility of the produced liquid/powder admixtures. Flow problems of such systems were addressed by the introduction of a new theoretical model for the principles underlying the formation of powdered solutions (3, 4). The developed mathematical expressions were shown to successfully allow for calculation of the optimum amounts of ingredients required to produce liquid/powder admixtures possessing, to a pre-specified desirable degree, acceptable flow characteristics.

In the same studies, a key concept termed flowable liquid-retention potential or $\Phi$-value (phi) of a powder was introduced and defined as the maximum amount of liquid that the unit weight of a powder material can retain inside its bulk while at the same time maintaining acceptable flowability. Moreover, $\Phi$-values of several powder excipients were determined using the "angle of slide" test to evaluate flow properties of liquid/powder admixtures containing light mineral oil as the incorporated liquid. The limit of acceptable flowability was set at an angle of slide equal to 33°. Criticism of that work was based on the facts that the "angle of slide" test does not necessarily represent a realistic evaluation of flow characteristics and that liquids other than light mineral oil should have been also used to test the powders.

In subsequent projects (5), acceptably flowing tablet formulations of clofibrate (liquid drug) and prednisolone (dissolved in a non-volatile solvent system), made according to the new mathematical flowability model, displayed consistently good flow properties and significantly higher dissolution profiles than those of commercial products, including soft gelatin capsule preparations. However, while evaluating the dissolution profiles of liquisolid tablets of clofibrate, compressibility problems were revealed. Specifically, such liquisolid formulations of clofibrate could not be compressed in to tablets of satisfactory hardness. While obtaining superior dissolution profiles of such "soft" clofibrate liquisolid tablets as compared to those of commercial soft gelatin capsules, an apparent plateau of their dissolution curves at the 80% level (cumulative percent of drug released versus time) was also observed. It has been concluded that this phenomenon occurred due to respective amounts of liquid drug being squeezed out of the liquisolid tablet during compression. Hence, even though the flowability model and the $\Phi$-value concept may ensure acceptable flow characteristics of liquisolid preparations, they have been proven inadequate to yield products possessing, to a pre-specified degree, acceptable compression properties.

For this reason, there is a need for a method of producing on an industrial scale, acceptably flowing and, simultaneously, compressible liquid/powder admixtures of liquid medications.

OBJECTS AND SUMMARY OF THE INVENTION

It is therefore an object of the present invention to provide a method of ensuring the consistent production of acceptably flowing and compressible liquid/powder admixtures of liquid medications.

It is also an object of the present invention to provide a means of optimizing the amounts of excipients required to yield such free-flowing and compressible liquid/powder admixtures.

The present invention is thus directed to a method of converting a liquid medication into a liquisolid system, wherein the liquid medication is incorporated into a specific amount of carrier material, and the resulting wet mixture is blended with a calculated amount of coating material to produce a "dry" (i.e. dry-looking), nonadherent, liquid/powder admixture which possesses acceptable flow and, simultaneously, acceptable compression characteristics.

A new formulation-mathematical model, which includes a redefined fundamental flow property of powders termed flowable liquid-retention potential ($\Phi$-value) and introduces a new fundamental compression property of powders termed compressible liquid-retention potential ($\Psi$-number), is provided to calculate the optimum amounts of carrier and coating materials required to yield such acceptably flowing and compressible liquid/powder admixtures.

Furthermore, two new testing procedures termed the "Liquisolid Flowability Test" and the "Liquisolid Compressibility Test" which are required to assess the $\Phi$-values and $\Psi$-numbers of powder excipients, are introduced.

Finally, various representative immediate and sustained release liquisolid tablet formulations and their flowability and compressibility evaluations and in-vitro and in-vivo release profiles compared to commercial products are included.

DETAILED DESCRIPTION OF THE DRAWINGS

DEFINITIONS

Figure 1:
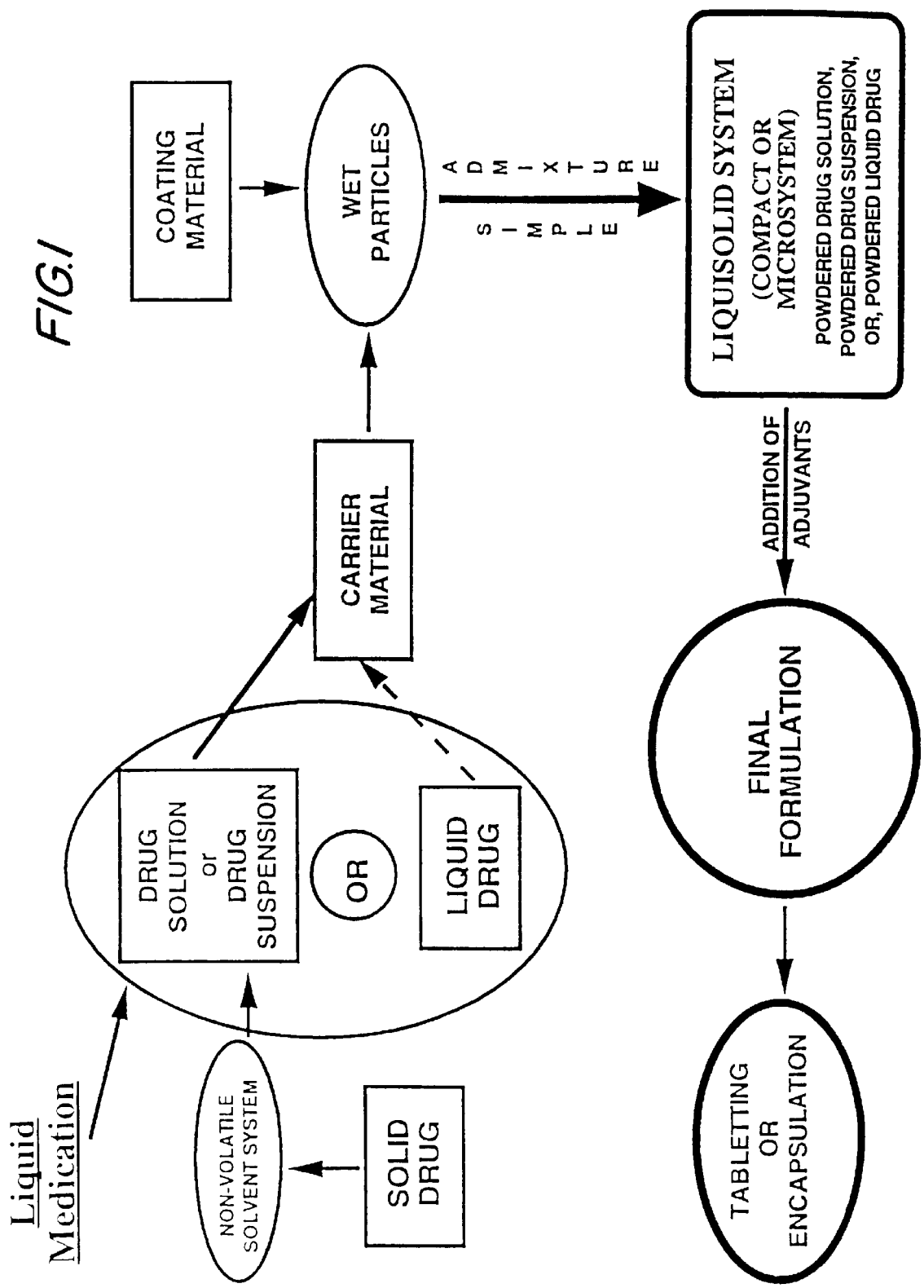
FIG. 1 is a schematic outline of steps involved in the preparation of liquisolid systems.

As used herein, the following terms have the meaning described below unless otherwise indicated:

The term "liquid medication" includes liquid lipophilic drugs and drug suspensions or solutions of solid water-insoluble drugs in suitable non-volatile solvent systems.

The term "water-insoluble drugs" includes those drugs that are "sparingly water-soluble" (1 part solute into 30 to 100 parts of water), "slightly water-soluble" (1 part solute into 100 to 1000 parts of water), "very slightly water-soluble" (1 part solute into 1000 to 10,000 parts of water), and "practically water-insoluble" or "insoluble" (1 part solute into 10,000 or more parts of water), as defined in USP XXII or Remington's Pharmaceutical Sciences.

The term "liquisolid systems" refers to powdered forms of liquid medications formulated by converting liquid lipophilic drugs, or drug suspensions or solutions of water-insoluble solid drugs in suitable non-volatile solvent systems, into "dry" (i.e., dry-looking), nonadherent, free-flowing and readily compressible powder admixtures by blending with selected carrier and coating materials. Based on the type of liquid medication contained therein, liquisolid systems may be classified into three subgroups: "powdered drug solutions," "powdered drug suspensions," and "powdered liquid drugs." The first two may be produced from the conversion of drug solutions (e.g., prednisolone solution in propylene glycol) or drug suspensions (e.g., gemfibrozil suspension in Polysorbate 80), and the latter from the formulation of liquid drugs (e.g., clofibrate, valproic acid, liquid vitamins, etc.), into liquisolid systems.

The term "liquisolid compacts" refers to immediate or sustained release tablets or capsules that are prepared using the technique described under "liquisolid systems," combined with the inclusion of appropriate adjuvants required for tabletting or encapsulation, such as lubricants, and for rapid or sustained release action, such as disintegrants or binders, respectively.

The term "liquisolid microsystems" refers to capsules prepared by the technique described under "liquisolid systems" combined with the inclusion of an additive, e.g., polyvinylpyrrolidone (PVP), in the liquid medication wherein the resulting unit size may be as much as five times less than that of liquisolid compacts.

The term "flowable liquid-retential potential" ($\Phi$-value) of a powder material describes its ability to retain a specific amount of liquid while maintaining good flow properties. The $\Phi$-value is defined as the maximum weight of liquid that can be retained per unit weight of the powder material in order to produce an acceptably flowing liquid/powder admixture.

The term "compressible liquid-retential potential" ($\Psi$-number) of a powder material describes its ability to retain a specific amount of liquid while maintaining good compression properties. The $\Psi$-number is defined as the maximum weight of liquid that can be retained per unit weight of the powder material in order to produce an acceptably compressible liquid/powder admixture, i.e., being able to yield tablets of satisfactory mechanical crushing strength (hardness) without presenting any liquid squeezing out of the liquisolid mass during compaction.

The term "pactisity" ($\Omega$) of a liquisolid system is the maximum crushing strength (hardness) of a one-gram tablet of the system compressed at standard pactisity conditions (SPC).

The term "plateau compressional force" is the force required to achieve maximum powder cohesiveness which, in turn, results in maximum tablet hardness.

The term "carrier material" refers to a preferably porous material possessing sufficient absorption properties, such as microcrystalline and amorphous cellulose, which contributes in liquid absorption.

The term "coating material" refers to a material possessing fine and highly adsorptive particles, such as various types of amorphous silicon dioxide (silica), which contributes in covering the wet carrier particles and displaying a dry-looking powder by adsorbing any excess liquid. These adsorptive particles have a particle size range of about 10 nm to 5,000 nm in diameter.

DETAILED DESCRIPTION OF THE PRESENTLY PREFERRED EMBODIMENTS

Liquisolid systems are acceptably flowing and compressible powdered forms of liquid medications. A schematic outline of steps involved in the preparation of liquisolid systems is provided in FIG. 1. As seen there, a liquid lipophilic drug (e.g., chlorpheniramine, clofibrate, valproic acid, water-insoluble vitamins, fish oil, etc.) can be converted into a liquisolid system without being further modified. On the other hand, if a solid water-insoluble drug (e.g., gemfibrozil, nifedipine, digoxin, digitoxin, polythiazide, hydrochlorothiazide, methylclothiazide, etoposide, spironolactone, prednisolone, prednisone, hydrocortisone, etc.) is formulated, it should be initially dissolved or suspended in a suitable non-volatile solvent system to produce a drug solution or drug suspension of desired concentration. Inert, high boiling point, preferably water-miscible and not highly viscous organic solvent systems (e.g., propylene glycol, liquid polyethylene glycols, polysorbates, glycerin, N,N-dimethylacetamide, fixed oils, etc.) are most suitable for this process.

Next, a certain amount of the prepared drug solution or suspension, or the liquid drug itself, is incorporated into a specific quantity of carrier material which should be preferably of a porous nature and possessing sufficient absorption properties. Materials with a porous surface and closely matted fibers in their interior, such as powder and granular grades of microcrystalline and amorphous cellulose, are most preferred as carriers. The resulting wet mixture is then converted into a dry-looking, nonadherent, free-flowing and readily compressible powder by the simple addition and mixing of a calculated amount of coating material. Excipients possessing fine and highly adsorptive particles, such as various types of amorphous silicon dioxide (silica), are most suitable for this step. Before compression or encapsulation, various adjuvants such as lubricants and disintegrants (immediate) or binders (sustained-release) may be mixed with the finished liquisolid systems to produce liquisolid compacts (tablets or capsules).

Based on the type of liquid medication contained therein, liquisolid systems may be classified into three subgroups: "powdered drug solutions," "powdered drug suspensions" and "powdered liquid drugs." The first two may be produced from the conversion of drug solutions or drug suspensions and the latter from the formulation of liquid drugs into liquisolid systems.

Based on the formulation technique used, liquisolid systems may be classified into two categories, namely, liquisolid compacts or liquisolid microsystems. The first are prepared using the previously outlined method to produce tablets or capsules, whereas the latter are based on a new concept which employs similar methodology combined with the inclusion of an additive, e.g., polyvinylpyrrolidone (PVP), in the liquid medication which is incorporated into the carrier and coating materials to produce an acceptably flowing admixture for encapsulation. The advantage stemming from this new technique is that the resulting unit size of liquisolid microsystems may be as much as five times less than that of liquisolid compacts.

Regarding "powdered drug solutions," it must be emphasized that their preparation is not a solvent deposition technique since it does not involve drying or evaporation. Since non-volatile solvents are used to prepare the drug solution or suspension, the liquid vehicle does not evaporate and thus, the drug is carried within the liquid system which in turn, is dispersed throughout the final product.

The production of liquisolid systems possessing acceptable flowability and compressibility has been addressed with the development of a new formulation-mathematical model, based on the new fundamental powder properties termed "flowable ($\Phi$-value) and compressible ($\Psi$-number) liquid retention potentials" of the constituent powders. According to the proposed theories, the carrier and coating materials can retain only certain amounts of liquid while maintaining acceptable flow and compression properties. Depending on the excipient or carrier:coating ratio (R) of the powder system used, which is the ratio between the quantities of carrier (Q) and coating (q) materials present in the formulation (R=Q/q), there is a characteristic maximum liquid load on the carrier material, termed "load factor" ($L_f$) and defined as the ratio of the amount of liquid medication (W) over the quantity of carrier material (Q) in the system ($L_f$=W/Q), which should be possessed by an acceptably flowing and compressible liquisolid system.

The two key properties of liquisolid powder excipients, namely, $\Phi$-value and $\Psi$-number, may be determined by two recently developed methods, termed "liquisolid flowability (LSF) and liquisolid compressibility (LSC) tests." In the LSF test, recording powder flowmetry is employed to assess and classify powder flow characteristics such as flow rate and consistency, whereas in the LSC test, a newly introduced powder compaction property termed "pactisity", $\Omega$, and the derived linear "pactisity equation" are used to classify compression characteristics of prepared liquisolid systems.

Following are the major process steps and calculations involved in the formulation of acceptably flowing and compressible liquisolid compacts:

1. If a solid water-insoluble drug is formulated, the drug is first dissolved or suspended in a non-volatile solvent (e.g., propylene glycol, polyethylene glycol 400, glycerin, polysorbate 80, sorbitan monolaurate, N,N, dimethylacetamide, fixed oils, other liquid surfactants, etc.) to produce a drug solution or drug suspension of certain composition (% w/w concentration).
2. The weight W (in grams) of drug solution or suspension or liquid drug required to be included in a single liquisolid compact unit possessing a desired strength of active ingredient is selected.
3. The carrier (e.g., cellulose) and coating (e.g., silica) materials to be included in the liquisolid formulation are selected.
4. The characteristic excipient or carrier:coating ratio $R_{min}$ (w/w) and the flowable liquid-retention potentials ($\Phi$-values, w/w) of the carrier ($\Phi$) and coating ($\phi$) materials are determined using the "Liquisolid Flowability (LSF) Test" as summarized below.
5. The compressible liquid-retention potentials ($\Psi$-numbers, w/w) of the carrier ($\Psi$) and coating ($\psi$) materials are determined using the "Liquisolid Compressibility (LSC) Test" as summarized below.
6. The desired excipient or carrier:coating ratio R, where $R>R_{min}$, of the carrier:coating combination to be included in the liquisolid system is selected. If minimum unit dose weight ($U_{min}$) is desired, the excipient ratio of the formulation must be selected to be equal to $R_{min}$ which is the characteristic minimum excipient ratio of the carrier:coating system used.

7. The optimum load factor $L_o$ (w/w) required to yield an acceptably flowing and compressible liquisolid system is assessed using Equations 1–4.

$$L_o = {}^\Phi L_f \text{ when } {}^\Phi L_f < {}^\Psi L_f \qquad \text{(Eq. 1)}$$

or $$L_o = {}^\Psi L_f \text{ when } {}^\Phi L_f > {}^\Psi L_f \qquad \text{(Eq. 2)}$$

where:

$${}^\Phi L_f = \Phi + \phi(1/R) \qquad \text{(Eq. 3)}$$

and $${}^\Psi L_f = \Psi + \psi(1/R) \qquad \text{(Eq. 4)}$$

If a powder system (carrier:coating) mixed at its minimum excipient ratio ($R_{min}$) has been selected, the required maximum load factor $L_{max}$ may be determined using Equations 5–8.

$$L_{max} = {}^\Phi L_{max} \text{ when } {}^\Phi L_{max} < {}^\Psi L_{max} \qquad \text{(Eq. 5)}$$

or $$L_{max} = {}^\Psi L_{max} \text{ when } {}^\Phi L_{max} > {}^\Psi L_{max} \qquad \text{(Eq. 6)}$$

where:

$${}^\Phi L_{max} = \Phi + \phi(1/R_{min}) \qquad \text{(Eq. 7)}$$

and $${}^\Psi L_{max} = \Psi + \psi(1/R_{min}) \qquad \text{(Eq. 8)}$$

8. Finally, the optimum quantities (in grams) of carrier ($Q_o$) and coating ($q_o$) materials required to be mixed with the desired amount W of liquid in order to produce an acceptably flowing and compressible liquisolid compact are determined using Equations 9 and 10, respectively.

$$Q_o = W/L_o \qquad \text{(Eq. 9)}$$

$$q_o = Q_o/R \qquad \text{(Eq. 10)}$$

The minimum carrier quantity ($Q_{min}$) and maximum coating ($q_{min}$) required to produce an acceptably flowing and compressible liquisolid compact unit possessing minimum weight ($U_{min}$) and containing an amount W of liquid may be assessed using Equations 11 and 12, respectively.

$$Q_{min} = W/L_{max} \qquad \text{(Eq. 11)}$$

$$q_{max} = Q_{min}/R_{min} \qquad \text{(Eq. 12)}$$

It must be pointed out that, in terms of producing compacts of realistic unit size, the practical substance of the liquisolid formulation desired to be prepared may be assessed by predicting its unit dose weight $U_w$ using Equation 13. This can be done as long as the weight W of the liquid medication (to be included in a single liquisolid compact unit) and the desired excipient ratio R of the formulation have been selected leading to the determination of the required optimum load factor $L_o$. The minimum possible unit dose weight $U_{min}$ which can be produced by the carrier:coating system may be also predicted using Equation 14, having selected the weight W of the liquid medication (per unit dose) and having determined the minimum excipient ratio $R_{min}$ of the powder system and its corresponding maximum load factor $L_{max}$ required to yield a flowable and compressible liquisolid system.

$$U_w = W + W(1 + 1/R)(1/L_o) \qquad \text{(Eq. 13)}$$

$$U_{min} = W + W(1 + 1/R_{min})(1/L_{max}) \qquad \text{(Eq. 14)}$$

The formulation steps and mathematical expressions employed to calculate the optimum amounts of carrier and coating materials to produce acceptably flowing and compressible liquisolid systems have been compiled in Table 1.

Liquisolid Flowability (LSF) Test

A test method, called the liquisolid flowability (LSF) test, was developed and employed to determine the flowable liquid retention potential ($\Phi$-value) of several powder excipients likely to be included in liquisolid compacts. The test is basically a titration-like procedure in which 25 to 30 grams of mixtures of the powders under investigation, with increasing amounts of a non-volatile solvent (i.e., liquid/solid weight composition), such as, for example, propylene glycol, polyethylene glycol, light mineral oil and clofibrate, are prepared using a standard mixing process which ensures uniformity, and their flow rate and consistency are assessed using a recording powder flowmeter (RPF). The liquid/solid weight composition (w/w) in that admixture which just complies with a desired and pre-selected limit of acceptable flowability, is taken as the $\Phi$-value of the excipient. Accordingly, the liquid/powder admixture with liquid content slightly higher than the $\Phi$-value of the powder material should not be flowing within the desired limit of acceptable flow. It should be noted that the non-volatile solvent used in the LSF test should be the one selected to be included in the liquid medication (drug solution or drug suspension) of the targeted liquisolid product; where a liquid drug is formulated, then the LSF test should be conducted with the liquid drug itself.

Basically, the method consists of the following steps:

a. Preparing several powder systems each containing a carrier material and a coating material and selecting for each system a carrier:coating ratio, $R_1 \ldots _x$, where $_1 \ldots _x$ corresponds to the powder systems prepared, $R_1 \ldots _x = Q_1 \ldots _x/q_1 \ldots _x$, $Q_1 \ldots _x$=the weight of the carrier material, and $q_1 \ldots _x$=the weight of the coating material, such that, $R_1 = Q_1/q_1$, $R_2 = Q_2/q_2$, $R_3 = Q_3/q_3 \ldots R_x = Q_x/q_x$;

b. Preparing several uniform liquid/powder admixtures of different liquid/solid weight compositions ($C_w$) by combining one of the powder systems prepared in step (a) with increasing amounts of a non-volatile solvent, wherein the non-volatile solvent is selected from that which is to be included in the liquid medication (drug solution, drug suspension), or the liquid drug itself, of the targeted liquisolid product;

c. Assessing the flow rate and consistency of the admixtures thus obtained using a recording powder flowmeter and determining from this assessment the flowable liquid load factor ($^\Phi L_f$) of the powder system which complies with a preselected limit of acceptable flowability, where $^\Phi L_f = W/Q$, W=the weight of the liquid and Q=the weight of the carrier material;

d. Repeating steps (b) and (c) for the remaining powder systems of step (a) to determine the flowable liquid load factors of these systems; and e. Plotting the flowable liquid load factors ($^{\Phi}L_f$) thus obtained against the corresponding reciprocal carrier:coating ratios (1/R) of the powder systems, thereby obtaining a linear plot having a Y-intercept equal to the flowable liquid-retention potential (Φ-value) of the carrier material (Φ) and a slope equal to the flowable liquid-retention potential (Φ-value) of the coating material (φ).

The LSF test can be used not only for the preparation of acceptably flowing liquisolid compacts, but also for the general evaluation of the flowability of powders.

Limit of Acceptable Flowability

In the present studies, a powder, or a liquid/powder admixture, was considered as possessing acceptable flow properties, if 25 to 30 grams of the liquid/powder sample was able to pass through the hopper of the RPF assembly (at a vibration level produced by a standard pressure of 10 psi) exhibiting a flow rate not less than 4 grams/sec and flow consistency without any blockages at the start or during the powder flow. Since the objective of these studies was to investigate the Φ-value concept in a comparative fashion, the line of acceptable flow was drawn in a more or less arbitrary manner. The above conditions were chosen based on results of preliminary work indicating that the powder flow of model formulations was satisfactory on a Zanasi LZ-64 capsule machine (Zanasi Co., Bologna, Italy). When selecting another machine, however, the limits of acceptable flowability should be calibrated and adjusted to the requirements of that specific piece of equipment. Consequently, by altering the limits of acceptable flow, the same powders might display different Φ-values.

Liquisolid Compressibility (LSC) Test

A test method, called the liquisolid compressibility (LSC) test, was developed and employed to determine the compressible liquid-retention potential, i.e., Ψ-number, of several powder excipients likely to be included, as carrier or coating materials, in liquisolid compacts. Basically, the method consists of the following steps:

a. Preparing several powder systems each containing a carrier material and a coating material and selecting for each system a carrier:coating ratio, $R_{1 \ldots x}$, where $_{1 \ldots x}$ corresponds to the powder systems prepared,
$R_{1 \ldots x} = Q_{1 \ldots x}/q_{1 \ldots x}$,
$Q_{1 \ldots x}$=the weight of the carrier material, and
$q_{1 \ldots x}$=the weight of the coating material,
such that, $R_1=Q_1/q_1$, $R_2=Q_2/q_2$, $R_3=Q_3/q_3$ ... $R_x=Q_x/q_x$;

b. Preparing several uniform liquid/powder admixtures of different liquid/solid weight compositions ($C_w$) by combining one of the powder systems prepared in step (a) with increasing amounts of a non-volatile solvent, wherein the non-volatile solvent is selected from that which is to be included in the liquid medication (drug solution, drug suspension), or the liquid drug itself, of the targeted liquisolid product;

c. Compressing each liquid/powder admixture thus obtained into tablets of certain weight using plateau compressional force to achieve maximum tablet crushing strength;

d. Assessing the average tablet crushing strength, $S_c$, of the tablets produced and calculating their pactisity, Ω, where $\Omega = S_c W_t$ and $W_t$=the average tablet weight in grams;

e. Determining the average liquid content of the crushed tablets and calculating the net liquid/solid weight composition ($C_w$) of the crushed liquid/powder admixture;

f. Determining the characteristic intrinsic pactisity, $\Omega_c$, and sponge index, $\sigma_i$, of the powder system by plotting the data obtained as log Ω versus $C_w$, where log $\Omega = \log\Omega_o - \sigma_i \cdot C_w$;

g. Determining the $\Psi_{mix}$, which is the compressible liquid retention potential (Ψ-number) of the powder system, where $\Psi_{mix} = (\log \Omega_o - \log 20)/\sigma_i$;

h. Determining the compressible liquid-load factor ($^{\Psi}L_f$) of the powder system, where $^{\Psi}L_f = \Psi_{mix}(1+1/R)$;

i. Repeating steps (b) through (h) for the remaining powder systems of step (a) to determine their compressible liquid load factors; and j. Plotting the compressible liquid load factors thus obtained against the corresponding reciprocal carrier:coating ratios (1/R) of the powder systems, thereby obtaining a linear plot having a Y-intercept equal to the compressible liquid-retention potential (Ψ-number) of the carrier material (Ψ) and a slope equal to the compressible liquid-retention potential (Ψ-number) of the coating material (ψ).

Therefore, the Ψ-number of a powder represents a certain liquid/solid content (w/w) $C_w$ that when compressed at plateau pressures, termed standard pactisity conditions, will yield a compact possessing a pactisity Ω equal to 20 kg/g.

The LSC test can be used not only for the preparation of acceptably compressible liquisolid compacts, but also for the general evaluation of the compactibility of powder excipients and formulations. Compared to current methods of "compaction simulation," the LSC test is simple, accurate and reproducible.

TABLE 1

Formulation and Mathematical Model of Liquisolid Systems

| Formulation Steps: | Optimum Load Factor $L_o$ | |
|---|---|---|
| Selection of the weight (W) of drug solution or liquid drug | $L_o = {}^{\Phi}L_f$ when ${}^{\Phi}L_f < {}^{\Psi}L_f$ | Optimum Carrier and Coating Quantities |
| Selection of the carrier and coating powder materials | or | $Q_o = W/L_o$ and |
| Determination of Φ-value, Ψ-number and $R_{min}$ of powders | $L_o = {}^{\Psi}L_f$ when ${}^{\Phi}L > {}^{\Psi}L_f$ | $q_o = Q_o/R$ |
| Selection of desired excipient ratio (R) of the carrier:coating powder system (R > $R_{min}$) | where: ${}^{\Phi}L_f = \Phi + \phi(1/R)$ | Prediction of Unit Dose Weight ($U_w$) |
| Determination of the optimum | and | |

TABLE 1-continued

Formulation and Mathematical Model of Liquisolid Systems

| Formulation Steps: | Optimum Load Factor $L_o$ |
| --- | --- |
| load factor ($L_o$) of formulation Determination of the optimum quantities of carrier ($Q_o$) and coating ($q_o$) materials | $^\Psi L = \Psi + \psi(1/R)$ $\quad U_w = W + W(1 + 1/R)(1/L_o)$ |

Symbolism:
W, $Q_o$ and $q_o$: optimum quantities of liquid, carrier and coating materials, respectively.
$\Phi$ and $\phi$: flowable liquid retention potential ($\Phi$-value) of carrier and coating material.
$\Psi$ and $\psi$: compressible liquid retention potential ($\Psi$-number) of carrier and coating material.

Determined physical properties of powder excipients, i.e., $\Phi$-value, $\Psi$-number and $R_{min}$, essential to the formulation of flowable and compressible liquisolid compacts, and determined by the previously described LSF and LCS testing, are compiled in Table 2.

TABLE 2

Liquid Formulation Parameters of Various Powder Excipients

| | | Liquisolid Formulation Parameters[a] | | | | | |
| --- | --- | --- | --- | --- | --- | --- | --- |
| Powder | Minimum | $\Phi$ value (w/w) | | | $\Psi$-number (w/w) | | |
| Excipients or Systems | Excipient Ratio $R_{min}$ | PG | PEG 400 | CLF | PG | PEG 400 | CLF |
| Avicel PH 102 | | 0.16 | 0.005 | 0.00 | 0.224 | 0.242 | 0.086 |
| Avicel PH 200 | | 0.26 | 0.02 | 0.01 | 0.209 | 0.232 | 0.046 |
| E.G.C. | | 0.25 | — | — | 0.227 | — | — |
| Cab-O-Sil M5 (silica)[b] with Avicel PH 102 | 18 | 3.31 | 3.26 | 1.68 | 0.560 | 0.653 | 1.554 |
| Cab-O-Sil M5 (silica)[b] with Avicel PH 200 | 8 | 2.57 | 2.44 | 1.88 | 0.712 | 0.717 | 1.709 |
| Cab-O-Sil M5 (silica)[b] with E.G.C. | 7 | 3.44 | — | — | 0.881 | — | — |
| Syloid 244 FP (silica)[b] with Avicel PH 200 | 7 | 2.68 | — | — | 0.797 | — | — |

[a]$\Phi$ values, $\Psi$-numbers and $R_{min}$ determined using LSF, LSC and B-LSC tests (see chapters 2 & 3)
[b]Included as the coating material in carrier:coating powder systems; the carrier is written in italics.

Advantages of Liquisolid Systems

A great number of slightly and very slightly water-soluble and practically water-insoluble liquid and solid drugs, such as those previously mentioned, can be formulated into liquisolid systems using the new formulation-mathematical model. It is well established that better availability of an orally administered water-insoluble drug is achieved when the drug is in solution form. That is why soft gelatin capsules containing solubilized forms of such medications demonstrate higher bioavailability compared to conventional oral solid dosage forms. The same principle governs the mechanism of drug delivery from liquisolid systems, specifically, powdered drug solutions, and is chiefly responsible for the improved dissolution profiles exhibited by these preparations. In this instance, even though the drug is in a tabletted or encapsulated dosage form, it is held in a solubilized liquid state, which consequently contributes to increased drug wetting properties, thereby enhancing drug dissolution.

Another advantage of liquisolid systems is that their production cost is lower than that of soft gelatin capsules because the production of liquisolid systems is similar to that of conventional tablets. Still another possible advantage of liquisolid systems, particularly for powdered liquid drugs, should be mentioned. During dissolution of a liquisolid tablet, after the disintegration process is completed, the drug solution or liquid drug, carried on the suspended and thoroughly agitated primary particles, is dispersed throughout the volume of the dissolution medium; such a phenomenon does not extensively occur during the dissolution process of soft gelatin capsule preparations. Therefore, since more drug surface is exposed to the dissolving medium, liquisolid systems exhibit enhanced drug release.

Most liquid or solid "water-insoluble drugs" may be formulated into immediate-release or sustained-release "liquisolid compacts" or "liquisolid microsystems."

Optimized rapid-release liquisolid tablets or capsules of water-insoluble drugs exhibit enhanced in-vitro and in-vivo drug release as compared to their commercial counterparts, including soft gelatin capsule preparations, as illustrated in FIGS. 2–8.

Figure 9:
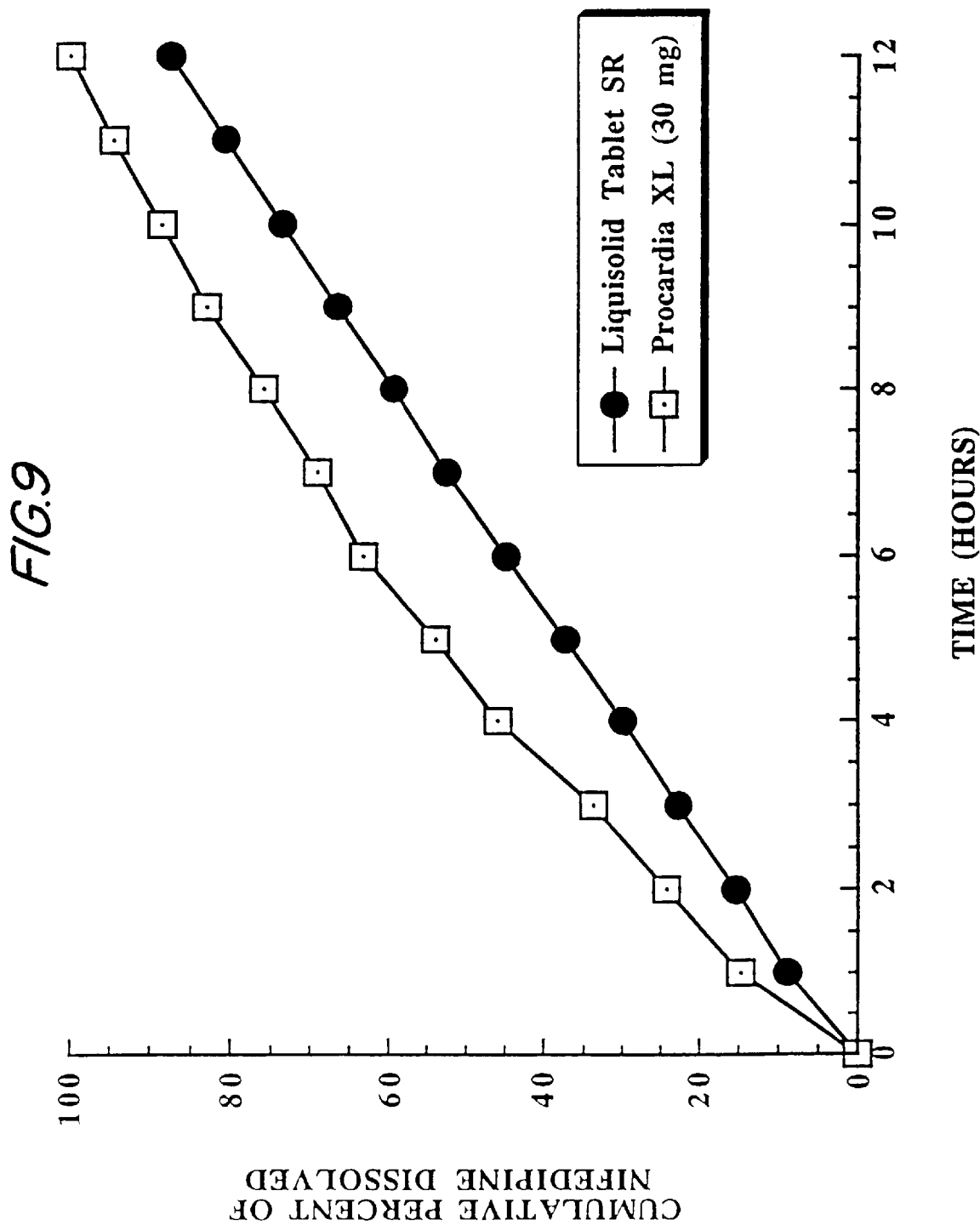
FIG. 9 is a graph showing the comparative dissolution profiles of nifedipine from (30 mg) sustained release liquisolid and commercial tablets.

Optimized sustained-release liquisolid tablets or capsules of water-insoluble drugs exhibit surprisingly constant dissolution rates (zero-order release) comparable only to expensive commercial preparations that combine osmotic pump technology and laser-drilled tablets, as illustrated in FIG. 9.

Testing of the Invention

The validity and applicability of the new mathematical model were tested by producing flowable and compressible systems containing various liquid medications. Liquisolid tablet formulations of the oil liquid drug, clofibrate, and of several water-insoluble solid drugs such as nifedipine, gemfibrozil, hydrocortisone, predinisolone, prednisone, spironolactone, methylclothiazide, and hydrochlorothiazide dissolved in suitable non-volatile solvents, were evaluated. Additionally, the in-vitro dissolution profiles of such liquisolid products were compared with those of their commercial counterparts. Furthermore, the effects of aging on the crushing strengths and dissolution profiles of prepared liquisolid tablets were also investigated. Finally, in-vivo studies were conducted in rats to compare clofibrate, nifedipine and gemfibrozil liquisolid compacts with their commercial counterparts.

Materials

The following materials were used as received; gembibrozil (Sigma Chem. Corp., St. Louis, Mo.); nifedipine (Barr Laboratories, Inc., Pomona, N.Y.); hydrochlorothiazide USP and hydrocortisone USP (Ciba-Geigy Co., Pharmaceuticals Division, Summit, N.J.); spironolactone USP, prednisolone USP and methyclothiazide USP (Geneva Pharmaceuticals, Inc., Broomfield, Colo.); prednisone USP (Amend, Drug & Chemical Co., Irvington, N.J.); clofibrate (Ayerst Laboratories, Inc., New York, N.Y.); propylene glycol (Sigma Chemical Co., St. Louis, Mo.); polyethylene glycol 400 and polysorbate 80 (Tween® 80) (Ruger Chemical Co., Inc., Irvington, N.J.); microcrystalline celluloses, i.e., Avicel® PH 102-granular MCC grade and Avicel® PH 200-coarse granular MCC grade (F.M.C. Corp., Princeton, N.J.); experimental grade of granular amorphous cellulose (E.G.C.) sodium starch glycolate (Explotab®) (Edward Mendell Co., Inc., Carmel, N.Y.); amorphous silicon dioxides, i.e., Cab-O-Sil® M5 (Cabot Corp., Tuscola, Ill.) and Syloid® 244 FP (C.W. Grace Co., Davison Chemical Division, Baltimore, Md.); hydroxypropylmethylcellulose (HPMC) with viscosity grade 15 cps (Shin-etsu Chemical Co., Tokyo, Japan); and polyvinylpyrrolidone (PVP) (ISP Chemical Co., Bound Brook, N.J.).

The following commercially available products were used for the purpose of drug dissolution profile comparisons with liquisolid tablet formulations: Hydrocortone® 10 mg hydrocortisone, MSD tablets (Merck, Sharp & Dohme, West Point, Pa.) prednisolone 5 mg tablets, USP (Rugby Laboratories, Rockville Centre, LI, N.Y.), Meticorten® 1 mg prednisone tablets, USP (Schering Corp., Kenilworth, N.J.), Deltasone® 5 mg prednisone tablets, USP (Upjohn Co., Kalamazoo, Mich.), Aldactone® 25 mg spironolactone tablets, USP (G.D. Searle & Co., Chicago, Ill.), Esidrix® 25 mg hydrochlorothiazide tablets, USP (Ciba-Geigy Co., Pharmaceuticals Division, Summit, N.J.), methylclothiazide 5 mg tablets, USP (Geneva Generics, Broomfield, Colo.), Atromid-S® 500 mg clofibrate soft gelatin capsules (Ayerst Laboratories, Inc., New York, N.Y.), Lopid 600 mg gemfibrozil tablets (Parke-Davis, Div. of Warner Lambert Co., Morris Plains, N.J.) and nifedipine 10 mg soft gelatin capsules (Block Pharmaceuticals, Newark, N.J.).

Major pharmacological and physicochemical properties (10) of the active ingredients used are briefly discussed below:

1. Hydrocortisone, the principal natural glucocorticoid in man, is a white to practically white, odorless, crystalline powder which melts at about 215° C., with some decomposition. It is very slightly soluble in water and ether, slightly soluble in chloroform; 1 gram of drug is soluble in 40 ml of alcohol.
2. Prednisolone, a glucocorticoid 4 times more potent than hydrocortisone, is a white to practically white, odorless, crystalline powder which melts at about 235° C., with some decomposition. It is very slightly soluble in water; 1 gram of drug is soluble in 30 ml of alcohol and in 180 ml of chloroform.
3. Prednisone, a glucocorticoid 3 to 5 times more potent than hydrocortisone, is a white to practically white, odorless, crystalline powder which melts at about 230° C., with some decomposition. It is very slightly soluble in water; 1 gram of drug is soluble in 150 ml of alcohol and in 200 ml of chloroform.
4. Spironolactone, a steroid acting as a competitive antagonist of aldosterone, is a light cream-colored to light tan crystalline powder with faint to mild mercaptan-like odor. It is practically insoluble in water, freely soluble in chloroform, soluble in alcohol and slightly soluble in fixed oils. It melts between 198° C. and 207° C. with decomposition.
5. Methyclothiazide, an orally effective diuretic and antihypertensive agent of the thiazide group, is a white to practically white crystalline powder which melts with decomposition at 220° C. It is tasteless and odorless or has a slight odor, and possesses a $pK_a$=9.4. It is freely soluble in acetone; 1 gram of drug is soluble in more than 10,000 ml of water, in 92.5 ml of alcohol, in more than 10,000 ml of chloroform and in 2,700 ml of ether.
6. Hydrochlorothiazide, an effective diuretic 10 times more potent than the prototype benzothiadiazine diuretic, chlorothiazide, is a white to practically white, odorless crystalline powder which melts at about 268° C. with decomposition. It displays a $pK_{a1}$=7.9 and a $pK_{a2}$=8.6. It is slightly soluble in water, freely soluble in sodium hydroxide solution and in dimethylformamide, sparingly soluble in methanol, and insoluble in ether and chloroform.
7. Clofibrate, an antilipidemic agent which significantly decreases the VLDL levels in persons with hypertriglyceridemia, is a stable, colorless to pale yellow liquid with a faint odor and characteristic taste. It has a boiling and decomposition point of 158–160° C. It is insoluble in water and soluble in alcohol, chloroform and other common organic solvents.
8. Gemfibrozil, an antilipidemic agent which is the drug of choice in the treatment of hypertriglyceridemia, consists of white crystals melting at about 61°. It has a very low aqueous solubility and is classified as a practically water-insoluble substance.
9. Nifedipine, a potent peripheral vasodilator, consists of yellow crystals melting at 174° C. It is practically water-insoluble, slightly soluble in alcohol and very soluble in acetone and chloroform. Special care should be taken during handling since nifedipine solutions are extremely light sensitive.

Methods

A. Preparation of Liquisolid Tablet Formulations

Liquisolid tablet formulations of hydrocortisone, prednisolone, prednisone, spironolactone, methyclothiazide, hydrochlorothiazide and clofibrate were prepared using various cellulosic carriers (i.e., Avicel® PH 102 and PH 200, and E.G.C.) and silica coating materials (i.e., Cab-O-Sil® M5 and Syloid® 244 FP). For "powdered drug solutions" or "powdered drug suspensions" (i.e., liquisolid compacts of solid drugs), non-volatile solvents, such as, for example, propylene glycol (PG), polyethylene glycol 400 (PEG) and polysorbate 80, were employed to prepare the incorporated drug solutions or suspensions having, in some instances, different drug concentrations (% w/w). The new mathematical model was used to calculate the optimum quantities of ingredients required (per unit dose) to yield acceptably flowing and compressible systems. Various amounts, ranging from 5% to 12% w/w, of the disintegrant sodium starch glycolate (Explotab®) were included in all formulations in order to produce immediate-release preparations. The finished liquid/powder admixtures were compressed into cylindrical tablets possessing a specific crushing strength equal to 15 kg/g.

Formulation and Calculation Steps

The major process steps and calculations involved in the formulation of liquisolid compacts are outlined in Table 1. Initially, the amount of drug solution or liquid drug (W) to be contained in a single liquisolid compact was selected along with the excipient ratio (R, where R>$R_{min}$) of the carrier and coating materials desired to be included in the system. Since the Φ-values, Ψ-numbers and $R_{min}$ of the selected powder system, compiled in Table 2, were already determined, the optimum load factor ($L_o$) and consequently, the optimum quantities of carrier ($Q_o$) and coating ($q_o$) materials (per unit dose) required to yield flowable and compressible liquisolid systems were assessed using Eqs. 1–4 and 9–10. Finally, the calculated liquid and powder quantities were mixed with a desired amount of sodium starch glycolate and compressed into cylindrical tablets.

Preparation of Drug Solutions and Suspensions

For liquisolid compacts of solid drugs, non-volatile solvents (such as PG, PEG 400 and polysorbate 80) were employed to prepare the drug solutions or suspensions having, in some instances, different drug concentrations (% w/w). The desired quantities of solid drug and selected solvent were accurately weighed in a 20 ml glass beaker and then heated to 80° C.–90° C. with constant stirring, until a homogeneous drug solution was obtained. Selected amounts (W) of the resulting hot liquid medications were incorporated into calculated quantities of carrier and coating materials.

Example of Calculations

Objective: To calculate the quantities $Q_o$ and $q_o$ of Avicel® PH 200 (cellulosic carrier) and Cab-O-Sil® M5 (silica coating), respectively (at R=10), required in a single liquisolid tablet containing 10 mg of hydrocortisone in the form of 0.1 g of its 10% w/w drug solution in propylene glycol (i.e., W=0.1 g). According to previous determinations, compiled in Table 2 and related to experiments conducted using PG as the incorporated liquid, Avicel® PH 200 possesses a Φ=0.26 w/w and a Ψ=0.209 w/w, whereas Cab-O-Sil® M5, used as the coating in powder systems containing Avicel PH 200 as the carrier, possesses a φ=2.57 w/w and ψ=0.712 w/w. The minimum excipient ratio $R_{min}$ of an acceptably flowing Avicel® PH 200:Cab-O-Sil® M5 system has been found equal to 8 and thus, the selected formulation excipient ratio (R=10) fulfills the $R \geq R_{min}$ condition. Using Eqs. 1–4, the optimum load factor $L_o$ of the above liquisolid system may be calculated as follows:

$$^\Phi L_f = 0.26 + 2.57(1/10) = 0.517 \text{ and } ^\Psi L_f = 0.21 + 0.712(1/10) = 0.28$$

and since:

$$^\Phi L_f \geq {}^\Psi L_f,$$

then:

$$L_o = {}^\Psi L_f,$$

therefore:

$$L_o = 0.28 \text{ w/w}.$$

Hence, knowing the required value of $L_o$ for the selected excipient ratio of the powder system (R=10) and that each liquisolid tablet should contain a weight of drug solution (W) equal to 0.1 g, the optimum quantities ($Q_o$ and $q_o$, per unit dose) of carrier and coating materials may be calculated using Eqs. 9 and 10 as follows:

$$Q_o = 0.1/0.28,$$

thus:

$$Q_o = 0.357 \text{ g of Avicel® PH 200 per tablet,}$$

and, $$q_o b = 0.357/10,$$

thus:

$$q_o = 0.036 \text{ g of Cab-O-Sil® M5 per tablet.}$$

Mixing Process

A standard mixing process was used for all preparations. Initially, the calculated ingredient quantities per unit dose, multiplied by a factor equal to 50 (to prepare 50-tablet batches), were accurately weighed in a plastic weighing boat. Then, the liquid-powder contents, weighing 25 to 35 grams, were blended in a porcelain mortar with the aid of a pestle avoiding excessive trituration and particle size reduction. The mixing procedure was conducted in three stages. During the first stage, the system was blended at an approximate mixing rate of one rotation per second for approximately one minute in order to evenly distribute the liquid medication into the powder. In the second mixing stage, the liquid/powder admixture was evenly spread as a uniform layer on the surfaces of the mortar and left standing for approximately five minutes to allow the drug solution or liquid drug to be absorbed in the interior of the powder particles. In the third stage, the powder was scraped off the mortar surfaces by means of an aluminum spatula, and then blended with a calculated quantity (5% to 12% w/w) of the disintegrant, Explotab®, for another thirty seconds, in a manner similar to the one used in the first stage, producing the final liquisolid formulation to be compressed.

Compression Process

The prepared liquisolid systems were manually compressed into cylindrical tablets of desired weight using a model B hydraulic Carver Laboratory Press (Fred S. Carver, Inc., Hydraulic Equipment, Summit, N.J.). Round, flat-face punches and die units possessing diameters varying, according to intended tablet size, from 11/32" to 16/32" were used. All formulations were compressed into tablets possessing similar specific crushing strength, i.e., 15 kg/g. Specific crushing strength of a tablet is the ratio of its crushing strength $S_c$ (hardness) over its weight $W_t$, i.e., $S_c/W_t$. For instance, liquisolid tablets weighing 0.6 and 0.3 grams were compressed to a hardness ($S_c$) of 9 kg (i.e., 15 kg/g×0.6 g) and 4.5 kg (i.e., 15 kg/g×0.3 g), respectively.

B. Examples of Prepared Liquisolid Tablet Formulations

Hydrocortisone 5 and 10 mg Liquisolid Tablets (HSN)

Four liquisolid tablet formulations of hydrocortisone, denoted as HSN-1, HSN-2, HSN-3, and HSN-4, were prepared. Formulation HSN-1 contained 5 mg of hydrocortisone (per tablet) in the form of 0.15 g of its 3.33% w/w solution in PG, mixed with an E.G.C.:Cab-O-Sil® M5 system possessing an excipient ratio equal to 10. Formulations HSN-1 and HSN-2 contained 10 mg of hydrocortisone (per tablet) in the forms of 0.15 g of its 6.66% w/w solution and 0.1 g of its 10% w/w solution in PG, respectively. In both preparations, an Avicel® PH 200:Cab-O-Sil® M5 powder system was included at an excipient ratio equal to 10. Finally, formulation HSN-4 contained 10 mg of hydrocortisone (per tablet) in the form of 0.1 g of its 10% w/w solution in PG, mixed with an Avicel® PH 102:Cab-O-Sil® M5 powder combination possessing excipient ratio equal to 20. A 12% w/w of the disintegrant Explotab® was included in all liquisolid compacts. The prepared hydrocortisone tablet formulations are listed in Table 3.

Prednisolone 5 mg Liquisolid Tablets (PLN)

Four liquisolid tablet formulations of prednisolone, denoted as PLN-1, PLN-2, PLN-3 and PLN-4, were prepared. All systems contained 5 mg of prednisolone (per tablet) in the form of 0.108 g of its 4.63% w/w solution in PG, and various carrier:coating combinations. Specifically, the powder systems Avicel® PH 102:Cab-O-Sil® M5 (at $R=R_{min}=18$), Avicel® PH 200:Cab-O-Sil® M5 ($R_{min}=8$), Avicel® PH 200:Syloid® 244 FP ($R_{min}=7$) and E.G.C.:Cab-O-Sil® M5 ($R_{min}=7$) were included at their minimum excipient ratios in formulations PLN-1, PLN-2, PLN-3 and PLN-4, respectively. A 12% w/w of Explotab® was included in all liquisolid compacts. The prepared prednisolone tablet formulations are listed in Table 4.

TABLE 3

Liquisolid table (formulations of hydrocortisone (HSN 5 & 10 mg).

| Formulation Ingredients | Liquisolid Formulations (quantity/tablet in grams) | | | |
|---|---|---|---|---|
| | HSN-1 (5 mg) | HSN-2 (10 mg) | HSN-3 (10 mg) | HSN-4 (10 mg) |
| Drug solution 3.33% w/w (hydrocortisone in propylene glycol) | 0.150 g | — | — | — |
| Drug solution 6.67% w/w (hydrocortisone in propylene glycol) | — | 0.150 g | — | — |
| Drug solution 10% w/w (hydrocortisone in propylene glycol) | — | — | 0.100 g | 0.100 g |
| Avicel PH 102 (granular MCC) | — | — | — | 0.397 g |
| Avicel PH 200 (coarse gran. MCC) | — | 0.530 g | 0.357 g | — |
| E.G.C. (granular amorphous cellulose) | 0.477 g | — | — | — |
| Cab-O-Sil M5 (silica nm-sized) | 0.048 g | 0.053 g | 0.036 g | 0.020 g |
| Explotab (sodium starch glycolate) | 0.092 g | 0.100 g | 0.067 g | 0.071 g |
| Tablet Weight (grams) | 0.767 g | 0.833 g | 0.560 g | 0.588 g |

TABLE 4

Liquisolid tablet formulations of prednisolone (PLN 5 mg).

| Formulation Ingredients | Liquisolid Formulations (quantity/tablet in grams) | | | |
|---|---|---|---|---|
| | PLN-1 (5 mg) | PLN-2 (5 mg) | PLN-3 (5 mg) | PLN-4 (5 mg) |
| Drug solution 4.63% w/w (prednisolone in propylene glycol) (0.108 g for 5 mg PLN/tablet) | 0.108 g | 0.108 g | 0.108 g | 0.108 g |
| Avicel PH 102 (granular MCC) | 0.423 g | — | — | — |
| Avicel PH 200 (coarse gran. MCC) | — | 0.363 g | 0.334 g | — |
| E.G.C. (granular amorphous cellulose) | — | — | — | 0.306 g |
| Cab-O-Sil M5 (silica nm-sized) | 0.024 g | 0.045 g | — | 0.044 g |
| Syloid 244 FP (silica micron-sized) | — | — | 0.048 g | — |
| Explotab (sodium starch glycolate) | 0.076 g | 0.070 g | 0.067 g | 0.063 g |
| Tablet Weight (grams) | 0.631 g | 0.586 g | 0.557 g | 0.521 g |

Prednisone 1 and 5 mg Liquisolid Tablets (PSN)

Two liquisolid tablet formulations of prednisone possessing different strengths, i.e., 1 mg and 5 mg of prednisone per tablet, denoted as PSN-1 and PSN-2, were prepared. Both systems consisted of a mixture of Avicel® PH 200:Cab-O-Sil® M5 at an excipient ratio equal to 10, and different amounts (per tablet) of the same prednisone solution in PG possessing a standard 5% w/w drug concentration. Specifically, each PSN-1 tablet contained 1 mg of prednisone in the form of 0.02 g of its 5% w/w drug solution, whereas PSN-2 tablets contained 5 mg of drug in the form of 0.1 g of its 5% w/w drug solution in PG. In both liquisolid compacts a 12% w/w of Explotab® was included. The prednisone formulations are listed in Table 5.

Spironolactone 10 mg Liquisolid Tablets (SPN)

One liquisolid tablet formulation of spironolactone, denoted as SPN-1, was prepared. The system contained 10 mg of spironolactone (per tablet) in the form of 0.1 g of its 10% w/w solution in PEG 400, and a powder system of Avicel® PH 102:Cab-O-Sil® M5 possessing an excipient ratio equal to 20. A 12% w/w of Explotab® was also included. The prepared spironolactone liquisolid formulation is listed in Table 5.

Hydrochlorothiazide 25 mg Liquisolid Tablets (HTZ)

One liquisolid tablet formulation of hydrochlorothiazide, namely, HTZ-1, was prepared. The system contained 25 mg of hydrochlorothiazide (per tablet) in the form of 0.1 g of its 25% w/w solution in PEG 400, and a powder system of Avicel® PH 200:Cab-O-Sil® M5 possessing an excipient ratio equal to 10. A 12% w/w of Explotab® was also included. The prepared HTZ-1 formulation is listed in Table 5.

TABLE 5

Liquisolid tablet formulations of prednisone (PSN 1 & 5 mg), spironolactone (SPN 10 mg) and hydrochlorothiazide (HTZ 25 mg).

| Formulation Ingredients | Liquisolid Formulations (quantity/tablet in grams) | | | |
|---|---|---|---|---|
| | PSN-1 (1 mg) | PSN-2 (5 mg) | SPN-1 (10 mg) | HTZ-1 (25 mg) |
| Prednisone solution 5% w/w (in propylene glycol) | 0.020 g | 0.100 g | — | — |

TABLE 5-continued

Liquisolid tablet formulations of prednisone (PSN 1 & 5 mg), spironolactone (SPN 10 mg) and hydrochlorothiazide (HTZ 25 mg).

| Formulation Ingredients | Liquisolid Formulations (quantity/tablet in grams) | | | |
|---|---|---|---|---|
|  | PSN-1 (1 mg) | PSN-2 (5 mg) | SPN-1 (10 mg) | HTZ-1 (25 mg) |
| Spironolactone solution 10% 10% w/w (in polyethylene glycol-100) | — | — | 0.100 g | — |
| Hydrochlorothiazide solution 25% w/w (in polyethylene glycol-100) | — | — | — | 0.100 g |
| Avicel PH 102 (granular MCC) | — | — | 0.595 g | — |
| Avicel PH 200 (coarse gram, MCC) | 0.071 g | 0.357 g | — | 0.379 g |
| Cab-O-Sil M5 (silicon nm-sized) | 0.007 g | 0.036 g | 0.030 g | 0.038 g |
| Explotab (sodium starch glycolate) | 0.022 g | 0.067 g | 0.099 g | 0.071 g |
| Tablet Weight (grams) | 0.183 g | 0.560 g | 0.824 g | 0.580 g |

TABLE 6

Liquisolid tablet formulations of methyclothiazide (MTZ 5 mg) and clofibrate (CLF 50 & 100 mg).

| Formulation Ingredients | Liquisolid Formulations (quantity/tablet in grams) | | | |
|---|---|---|---|---|
|  | MTZ-1 (5 mg) | MTZ-2 (5 mg) | CLF-1 (100 mg) | CLF-2 (50 mg) |
| Methyclothizide solution 5% w/w (in polyethylene glycol-100) | 0.100 g | 0.100 g | — | — |
| Clofibrate (oily liquid drug) | — | — | 0.100 g | 0.050 g |
| Avicel PH 102 (granular MCC) | — | 0.595 g | — | 0.595 g |
| Avicel PH 200 (coarse gran. MCC) | 0.379 g | — | 0.505 g | — |
| Cab-O-Sil M5 (silica nm-sized) | 0.038 g | 0.030 g | 0.051 g | 0.030 g |
| Explotab (medium starch glycolate) | 0.071 g | 0.099 g | 0.035 g | 0.035 g |
| Tablet Weight (grams) | 0.588 g | 0.624 g | 0.691 g | 0.710 g |

Methyclothiazide 5 mg Liquisolid Tablets (MTZ)

Two liquisolid tablet formulations of methyclothiazide, denoted as MTZ-1 and MTZ-2, were prepared. Both systems contained 5 mg of methyclothiazide (per tablet) in the form of 0.1 g of its 5% w/w drug solution in PEG 400, and different carrier:coating systems. Specifically, the powder systems Avicel® PH 200:Cab-O-Sil® M5 (at R=10) and Avicel® PH 102:Cab-O-Sil® M5 (at R=20) were included in formulations MTZ-1 and MTZ-2, respectively. A 12% w/w of the disintegrant Explotab® was included in both liquisolid compacts. The prepared methylclothiazide tablet formulations are listed in Table 6.

Clofibrate 50 and 100 mg Liquisolid Tablets (CLF)

Two liquisolid tablet formulations of clofibrate, denoted as CLF-1 and CLF-2, were prepared. Formulation CLF-1 contained 100 mg of this oily liquid drug (per tablet) mixed with an Avicel® PH 200:Cab-O-Sil® M5 system possessing an excipient ratio equal to 10. On the other hand, formulation CLF-2 consisted of 50 mg clofibrate (per tablet) blended with an Avicel® PH 102:Cab-O-Sil® M5 combination possessing an excipient ratio equal to 20. A 5% w/w of the disintegrant Explotab® was included in both liquisolid compacts. The prepared clofibrate tablet formulations are listed in Table 6.

Gemfibrozil 60 mg Liquisolid Tablets (GFZ)

An optimized liquisolid tablet formulation of gemfibrozil, denoted as GF2, was prepared. It contained 60 mg of this practically water-insoluble drug (per tablet) in the form of 0.1 g of its 60% w/w suspension in polysorbate 80, mixed with an Avicel® PH 200:Cab-O-Sil® M5 system possessing an excipient ratio equal to 20 in the form of 0.1 g of its 60% w/w suspension in polysorbate 80. A 5% w/w of the disintegrant Explotab was included in the formulation which is listed in Table 7.

Nifedipine 10 mg Immediate Release Liquisolid Tablets (NFD-RR)

An optimized immediate release liquisolid tablet formulation of Nifedipine, denoted as NFD-RR was prepared. It contained 5 mg of this practically insoluble drug (per tablet) in the form of 0.1 g of its 5% w/w solution in polyethylene glycol 400, mixed with an Avicel® PH 200:Cab-O-Sil® M5 system possessing an excipient ratio equal to 20. A 5% w/w of the disintegrant Explotab was included in the formulation which is listed in Table 7.

Nifedipine 30 mg Sustained Release Liquisolid Tablets (NFD-SR)

An optimized immediate release liquisolid tablet formulation of Nifedipine, denoted as NFD-SR was prepared. It contained 30 mg of nifedipine in the form of 0.1 g of its 30% w/w suspension in PEG 400, mixed with an Avicel® PH 200:Cab-O-Sil® M5 system possessing an excipient ratio equal to 20. Twenty-two percent (22%) of the (matrix-producing) binder hydroxypropylmethyl cellulose (HPMC) and 5% of the lubricant magnesium stearate were included in the finished formulation which is listed in Table 7.

TABLE 7

Liquisolid tablet formulations of immediate release gemfibrozil (GFZ 60 mg) and nifedipine rapid release (NFD-RR 5 mg) and sustained release (NFD-SR 30 mg).

| Formulation Ingredients | Liquisolid Formulations (quantity/tablet in grams) | | |
|---|---|---|---|
|  | GFZ (60 mg) | NFD-RR (5 mg) | NFD-SR (30 mg) |
| Genfibrozil suspension 60% w/w (in polysorbate 80) | 0.100 g | — | — |
| Nifedipine solution 5% w/w (in polyethylene glycol-100) | — | 0.100 g | — |
| Nifedipine suspension 30% w/w (in polyethylene glycol-100) | — | — | 0.100 g |
| Avicel PH 200 (coarse gran. MCC) | 0.500 g | 0.392 g | 0.392 g |
| Cab-O-Sil M5 (silica nm-sized) | 0.025 g | 0.020 g | 0.020 g |
| Explotab (sodium starch glycolate) | 0.033 g | 0.028 g | — |
| HPMC (hydroxypropylmethylcellulose) | — | — | 0.154 |
| Magnesium Stearate (lubricant) | — | — | 0.034 |
| Tablet Weight (grams) | 0.658 g | 0.540 g | 0.700 g |

C. Dissolution Studies

An in-vitro release study of drugs from prepared liquisolid tablets and commercial products was performed using the USP/NF specifications (11) relevant to each drug preparation. Dissolution studies were conducted using a standard USP/NF VanderKamp dissolution apparatus (Van-Kel Industries, Inc., Chatham, N.J.) interfaced with a Beckman DU-37 automated dissolution testing spectrophotometer (Beckman Instruments Inc., Fullerton, Calif.). The various conditions employed during dissolution studies of products containing a particular drug, such as dissolution apparatus, rotational speed of the paddle or basket, type and volume of dissolution medium per vessel, spectrophotometric wavelength for drug analysis, etc., are listed in Table 8.

HSN-4 formulations were compressed using identical equipment, tooling and conditions, into 24 cylindrical tablets (each) possessing a diameter equal to $^{15}/_{32}"$. Standard

TABLE 8

List of various conditions employed during dissolution studies of
liquisolid tablets and commercial products of several medications.
Trade names, strengths and manufacturers of the tested marketed products are also included.

| Drug content of tested products | Apparatus (Method) | Rotational Speed (RPM) | Dissolution Medium (ml/vessel) | Maximum Wavelength (nm, UV range) | Commercial Products Compared |
|---|---|---|---|---|---|
| HYROCORTISONE | USP/NF II (paddle) | 50 rpm | Distilled Water (900 ml) | 247 nm | Hydrocortone 10 mg Tablets (merck Sharp & Dohme) |
| PREDNISOLONE | USP/NF II (paddle) | 50 rpm | Distilled Water (900 ml) | 245 nm | Prednisolone 5 mg Tablets (Rugby Laboratories) |
| PREDNISONE | USP/NF II (paddle) | 50 rpm | Distilled Water (500 ml) | 241 nm | Meticorten 1 mg (Schering) & Deltasone 5 mg Tablets (Upjohn) |
| SPIRONOLACTONE | USP/NF II (paddle) | 75 rpm | 0.1N HCl + 0.1% w/v SLS (1000 ml) | 241 nm | Aldactone 25 mg Tablets (Searle & Co.) |
| HYDROCHLOROTHIAZIDE | USP/NF I (basket) | 100 rpm | 0.1N HCl (900 ml) | 270 nm | Esidrix 25 mg Tablets (Ciba-Geigy) |
| METHYCLOTHIAZIDE | USP/NF II (paddle) | 50 rpm | 0.1N HCl (900 ml) | 268 nm | Methyclothiazide 5 mg Tablets (Geneva Generics) |
| CLOFIBRATE | USP/NF II (paddle) | 75 rpm | 0.5% w/v Tween 80 (1000 ml) | 278 nm | Atromid-S 500 mg Clofibrate Soft Gelatin Capsules (Ayersi) |

Six individual tablets or capsules from each product were tested. In all studies, the temperature of the dissolving medium was maintained at 37±0.5° C. Dissolution samples were automatically withdrawn at regular intervals using a Rabbit peristaltic pump (Rainin Instrument Co., Inc., Woburn, Mass.), prefiltered, filtered through a 0.45 μm nylon membrane, and analyzed spectrophotometrically (Table 8). After their assay, the dissolution samples were recirculated to their original vessels.

The spectrophotometric readings were converted into cumulative percent of drug released using the internal computation system of the Beckman DU-37 software, which was previously fed with the following parameters: (a) absorbance reading of a standard drug solution; (b) selected concentration of the standard drug solution measured; and (c) maximum concentration of the drug in the dissolution medium expected at the 100% release level. In preliminary studies, it was established that spectrophotometric quantitation was feasible since all drugs obeyed Beer's Law at the selected wavelengths and concentration ranges.

Finally, to ensure similar sink conditions during the dissolution process of prepared clofibrate liquisolid tablets, and since CLF-2 50 mg tablets contained only one-half the amount of clofibrate included in CLF-1 100 mg tablets, the dissolution studies of the CLF-2 tablet formulation were conducted by placing 2 tablets in each vessel. For the same reason, since CLF-1 liquisolid tablets contain 100 mg of clofibrate which is ⅕ of the amount found in the commercial soft gelatin capsule product (Atromid-S®-500 mg of clofibrate), the dissolution studies of the CLF-1 formulation were repeated by placing 5 clofibrate liquisolid tablets in each vessel. Results are included in FIG. 4.

D. Aging Studies

In an effort to obtain some idea on the stability of the liquisolid systems, the effects of aging on the dissolution profile and crushing strength of prepared hydrocortisone liquisolid tablets were investigated. Specifically, HSN-3 and HSN-4 formulations were compressed using identical equipment, tooling and conditions, into 24 cylindrical tablets (each) possessing a diameter equal to $^{15}/_{32}"$. Standard compression forces equal to 3,600 and 3,800 lbs were employed to produce HSN-3 and HSN-4 tablets, respectively. Moreover, similar compression rate (300 lbs/sec) and dwell time (1 sec) were used in all compactions. Twelve tablets from each formulation were stored under room conditions, and after 10 months their dissolution profiles and crushing strengths were determined using equipment and conditions similar to those previously employed to evaluate the fresh tablets. A comparison of the dissolution profile and tablet hardness values, obtained as an average of six determinations from fresh and aged hydrocortisone 10 mg liquisolid tablets, is presented in Table 9 and dissolution profiles plotted in FIG. 5.

TABLE 9

Comparison of dissolution profile and crushing strength of fresh
and aged (10 months) hydrocortisone 10 mg liquisolid tablets
(HSN-3 and HSN-4).

| | CUMULATIVE PERCENT DRUG RELEASED[a] | | | |
|---|---|---|---|---|
| TIME (minutes) | HSN-3 FRESH | HSN-3 AGED | HSN-4 FRESH | HSN-4 AGED |
| 5 | 88.7% (4.4) | 71.2% (2.8) | 89.5% (3.7) | 61.5% (2.3) |
| 10 | 97.6% (2.8) | 95.1% (1.5) | 98.2% (2.4) | 94.7% (1.6) |
| 15 | 99.4% (2.5) | 97.3% (1.2) | 100.1% (2.1) | 97.6% (1.0) |
| 20 | 100.2% (1.9) | 98.7% (1.4) | 101.2% (1.2) | 98.7% (0.9) |
| 30 | 101.3% (1.2) | 100.2% (0.9) | 102.1% (0.8) | 99.8% (0.5) |
| CRUSHING[a] STRENGTH (Tablet hardness) in kg | 8.23 kg (0.36) | 7.54 kg (0.52) | 8.75 kg (0.28) | 8.29 kg (0.35) |

[a]Average of six determinations. Standard deviation given in parenthesis.

E. Evaluation of the Proposed Mathematical Model

The capability of the proposed formulation and mathematical model to produce acceptably flowing and compressible liquisolid compacts was tested by assessing the flow and compression properties of several systems. New liquisolid formulations of hydrocortisone, methyclothiazide and clofibrate were prepared as described for the liquisolid tablets, but without the addition of a disintegrant.

Four liquisolid compacts, denoted as LC#1, LC#2, LC#3 and LC#4, containing 0.1 g (per compact unit) of a 10% w/w hydrocortisone solution in PG mixed with different carrier:coating combinations possessing minimum excipient ratios, were prepared. Specifically, Avicel® PH 102:Cab-O-Sil® M5 ($R_{min}$=18), Avicel® PH 200:Cab-O-Sil® M5 ($R_{min}$=8), Avicel® PH 200:Syloid® 244 FP ($R_{min}$=7) and E.G.C.:Cab-O-Sil® M5 ($R_{min}$=7) were used as the powder systems of formulations LC#1, LC#2, LC#3 and LC#4, respectively.

Furthermore, two liquisolid compacts, denoted as LC#5 and LC#6, containing 0.1 g (per compact unit) of a 5% w/w methyclothiazide solution in PEG 400 were prepared. The powder systems Avicel® PH 102: Cab-O-Sil® M5 ($R_{min}$=18) and Avicel® PH 200:Cab-O-Sil® M5 ($R_{min}$=8) possessing minimum excipient ratios were used to formulate LC#5 and LC#6, respectively. Finally, two more liquisolid compacts, denoted as LC#7 and LC#8, containing 50 and 100 mg (per compact unit) of clofibrate, respectively, were also prepared. The powder systems Avicel® PH 102:Cab-O-Sil® M5 ($R_{min}$=18) and Avicel® PH 200:Cab-O-Sil® M5 ($R_{min}$=8), were included at minimum excipient ratios in formulations LC#7 and LC#8, respectively.

The flowability and compressibility of the above liquisolid compacts were assessed by means of the flow rate and pactisity measurements which are described below. The prepared formulations along with their flow rate and pactisity determinations are presented in Tables 10 and 11.

TABLE 10

Flowability and compressibility evaluation of liquisolid compacts containing a solution of hydrocortisone in propylene glycol (10% w/w).

| Ingredients | LC #1 (HSN/PG) | LC #2 (HSN/PG) | LC #3 (HSN/PG) | LC #4 (HSN/PG) |
|---|---|---|---|---|
| Hydrocortisone solution in propylene glycol (10% w/w) | 0.100 g | 0.100 g | 0.100 g | 0.100 g |
| Avicel PH 102 (granular MCC) | 0.392 g | — | — | — |
| Avicel PH 200 (coarse gran. MCC) | — | 0.336 g | 0.311 g | — |
| E.G.C. (granular amorphous cellulose) | — | — | — | 0.283 g |
| Cab-O-Sil M5 (silica nm-sized) | 0.022 g | 0.042 g | — | 0.041 g |
| Syloid 244 FP (silica micron-sized) | — | — | 0.044 g | — |
| Compact Unit Weight (g) | 0.514 g | 0.478 g | 0.455 g | 0.424 g |
| Flow Rate (g/sec)[a] | 8.9 g/sec (0.7) | 10.8 g/sec (0.6) | 10.3 g/sec (0.5) | 9.2 g/sec (0.7) |
| Pactisity (kg/g)[b] | 22.1 kg/g (1.2) | 20.7 kg/g (1.1) | 21.4 kg/g (1.4) | 19.6 kg/g (1.1) |

[a]Average of 8 determinations. Standard deviation given in parenthesis. See text for flow rate determinations using the RRF method.
[b]Average of 6 determinations. Standard deviation given in parenthesis. See text for pactisity determinations using the LSC test.

TABLE 11

Flowability and compressibility evaluation of liquisolid compacts containing a solution of methyclothiazide in polyethylene glycol 400 (5% w/w) or clofibrate (oily liquid drug).

| Ingredients | LC #5 (MTZ/PEG-100) | LC #6 (MTZ/PEG-100) | LC #7 (Clofibrate) | LC #8 (Clofibrate) |
|---|---|---|---|---|
| Methyclothiazide solution in polyethylene glycol 400 (5% w/w) | 0.100 g | 0.100 g | — | — |
| Clofibrate (oily liquid drug) | — | — | 0.050 g | 0.100 g |
| Avicel PH 102 (granular MCC) | 0.537 g | — | 0.536 g | — |
| Avicel PH 200 (coarse gran. MCC) | — | 0.311 g | — | 0.408 g |
| Cab-O-Sil M5 (silica nm-sized) | 0.030 g | 0.039 g | 0.030 g | 0.051 g |
| Compact Unit Weight (g) | 0.667 g | 0.450 g | 0.616 g | 0.559 g |
| Flow Rate (g/sec)[a] | 6.7 g/sec (0.6) | 9.2 g/sec (0.4) | 5.1 g/sec (0.6) | 5.4 g/sec (0.3) |
| Pactisity (kg/g)[b] | 30.7 kg/g (1.1) | 21.3 kg/g (1.4) | 37.2 kg/g (2.1) | 24.9 kg/g (1.6) |

[a]Average of 8 determinations. Standard deviation given in parenthesis. See text for flow rate determinations using the RPF method.
[b]Average of 6 determinations. Standard deviation given in parenthesis. See test for pactisity determinations using the LSC test.

Flowability Evaluation

The flow rate and consistency of the prepared liquisolid systems were characterized using a recording powder flowmeter (RPF) assembly. Experimental conditions for flow rate determinations using the RPF were similar to those employed during the liquisolid flowability (LSF) test. Furthermore, the conditions characterizing a liquisolid system as acceptably flowing were similar to those set during LSF testing and Φ-value determinations. Consequently, a liquid/powder admixture was considered acceptably flowable if 30 grams of the mixture were able to pass through the hopper of the RPF assembly (at a vibration level produced by a standard pressure of 10 psi) exhibiting a flow rate of not less than 4 grams/sec and flow consistency without any blockages at the start or during the powder flow. Flow rates of prepared liquisolid tablet formulations, representing the average of 8 determinations, are given in Tables 10 and 11.

Compressibility Evaluation

The preparation liquisolid systems were manually compressed into cylindrical tablets of desired weight using a model B hydraulic Carver Laboratory Press (Fred S. Carver, Inc., Hydraulic Equipment, Summit, N.J.). Round, flat-face punches and die units of diameters varying from 13/32" to 15/32" were used. There were no inscriptions on the tooling. Standard pactisity conditions (SPC), i.e., plateau compression settings such as pressure of pactisity ($P_\Omega$) equal to 64,650 psi/g, pactisity pressure rate ($r_\Omega$) equal to 12,930 psi/g sec, and a pactisity pressure dwell time ($t_\Omega$) equal to 1 sec, were used during compression. The tabletting conditions corresponding to such SPC, i.e., maximum tabletting compression force ($F_t$) and tabletting compression rate ($r_t$), employed to compress a cylindrical liquisolid tablet possessing a desired weight $W_t$ and a diameter $D_t$ (die-diameter), were calculated using Eqs. 15 and 16.

$$F_t = (\pi/4) P_\Omega D_t^2 \quad \text{(Eq. 15)}$$

$$r_t = (\pi/4) r_\Omega W_t D_t^2 \quad \text{(Eq. 16)}$$

Using such SPC, six tablets from each system were compressed, and the pactisities ($\Omega$) of the liquisolid formulations were assessed and compared to the pactisity limit (i.e., $\Omega = 20$ kg/g) of acceptable compressibility. Specifically, 6 tablets from each formulation were first weighed and their average tablet weight, $W_t$, was recorded. Then, the tablets were crushed using a Schleuniger-2E tablet hardness tester and their average crushing strength, $S_c$, was assessed. Finally, the pactisity, $\Omega$, of the liquisolid system under investigation was calculated (in kg/g) using Eq. 17, i.e., $\Omega = S_c/W_t$. Pactisity $\Omega$ of a liquisolid compact is the crushing strength of a one-gram tablet of the system compressed at SPC. According to conditions defined during LSC testing, the liquisolid system under investigation was considered acceptably compressible if it could be compressed to a pactisity greater than or equal to 20 kg/g, without any visual evidence of liquid being squeezed out of the compacts during compression. Pactisity results of the prepared liquisolid compacts are included in Tables 10 and 11.

F. In Vivo Studies in Rats

In-vivo studies were conducted for testing liquisolid tablet formulations of clofibrate, gemfibrozil and nifedipine against their commercial counterparts. Male Sprague-Dawley rats (275–300 g) fasted overnight and were assigned to groups of six animals each. All dosings, defined in FIGS. 6, 7 and 8, were orally administered. Blood samples were collected at specified intervals and analyzed using RP-HPLC methods.

RESULTS AND DISCUSSION

The measured flow rates and pactisities of the liquisolid compacts LC #1–8 are given in Tables 10 and 11. All systems prepared according to the formulation-mathematical model of the present invention displayed acceptable flow and compression properties. Tested using the RPF assembly, all preparations exhibited flow rates higher than 4 g/sec and consistent flow without any blockages at the start or during the powder's passage through the hopper orifice. Moreover, the same liquid/powder admixtures, compressed at standard pactisity conditions (SPC), yielded pactisities greater than, or close to 20 kg/g. Such flow rate and pactisity results comply with the previously set limits of acceptable flowability and compressibility, providing verification for the validity of the mathematical model to produce free-flowing and readily compressible liquisolid systems.

Figure 2:
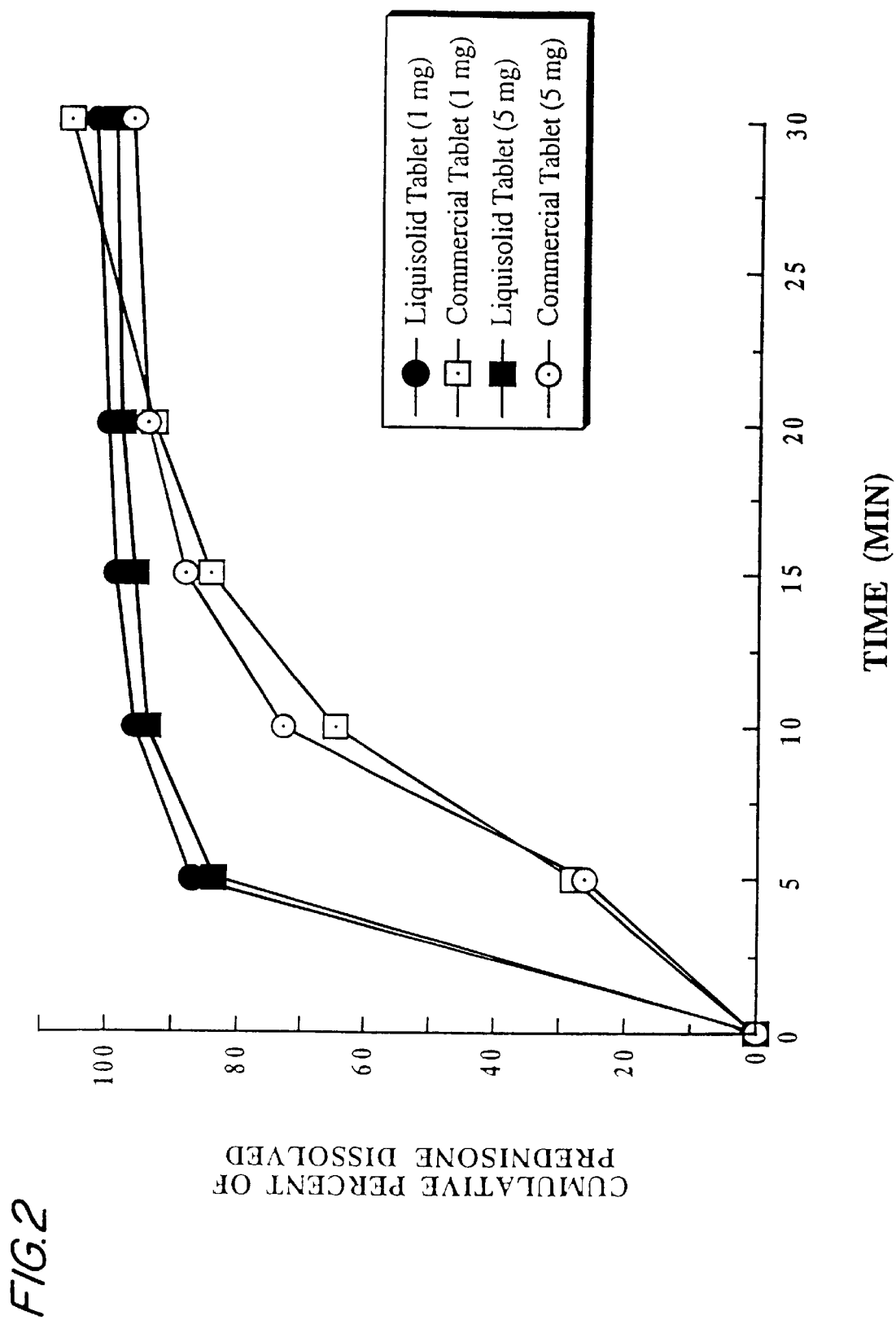
FIG. 2 is a graph showing the comparative dissolution profiles of prednisone from (1 mg and 5 mg) immediate-release liquisolid and commercial tablets.
Figure 3:
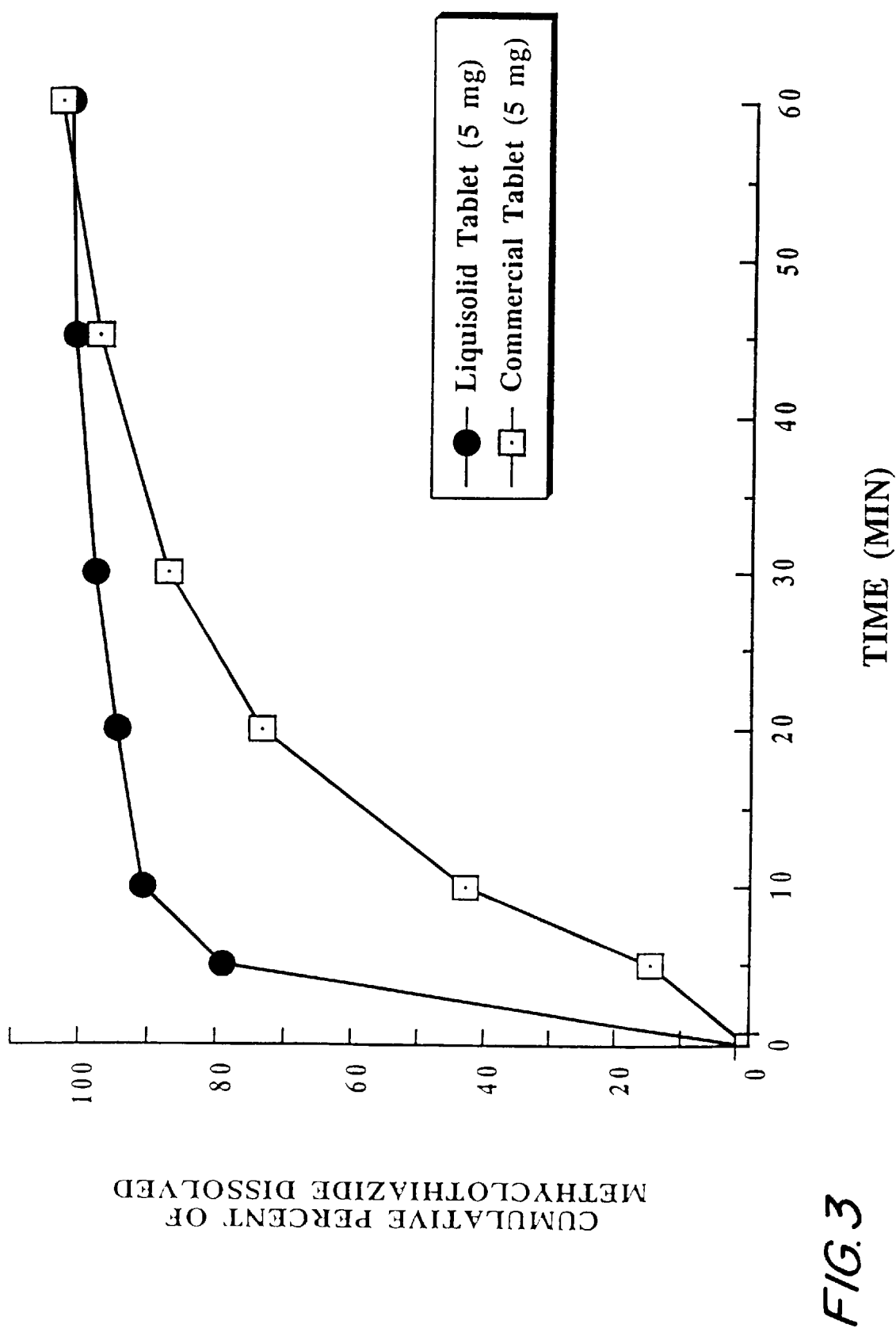
FIG. 3 is a graph showing the comparative dissolution profiles of methylclothiazide from (5 mg) immediate-release liquisolid and commercial tablets.
Figure 4:
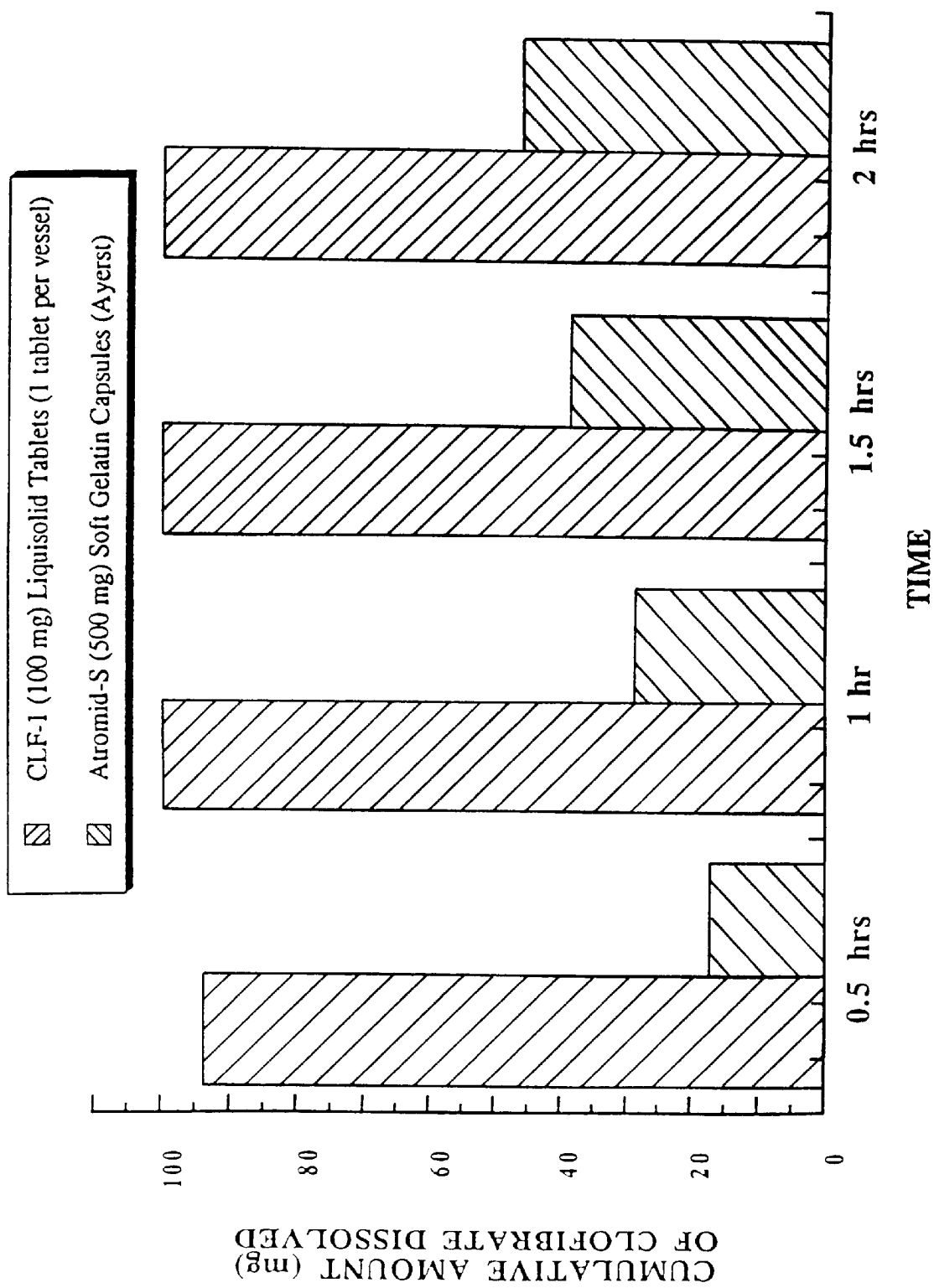
FIG. 4 is a graph showing the comparison of mean cumulative amounts of clofibrate released from immediate-release 100 mg liquisolid tablets and 500 mg commercial soft gelatin capsules.

Comparisons between the drug dissolution profiles of liquisolid tablets and their commercial counterparts are illustrated in FIGS. 2–4. As shown there, the prepared liquisolid tablets not only exceeded USP dissolution requirements but often yielded significantly higher drug release rates than those of their commercial counterparts.

In general, it has been observed that the drug release superiority of liquisolid tablets is inversely proportional to the aqueous solubility of the contained drug. Accordingly, the most impressive difference in dissolution profiles was shown in the case of the liquid lipophilic clofibrate where, within the first hour of dissolution, 100% of the drug was released from the liquisolid tablets but only 6% of the drug was released from the costly commercial soft gelatin capsules.

Figure 6:
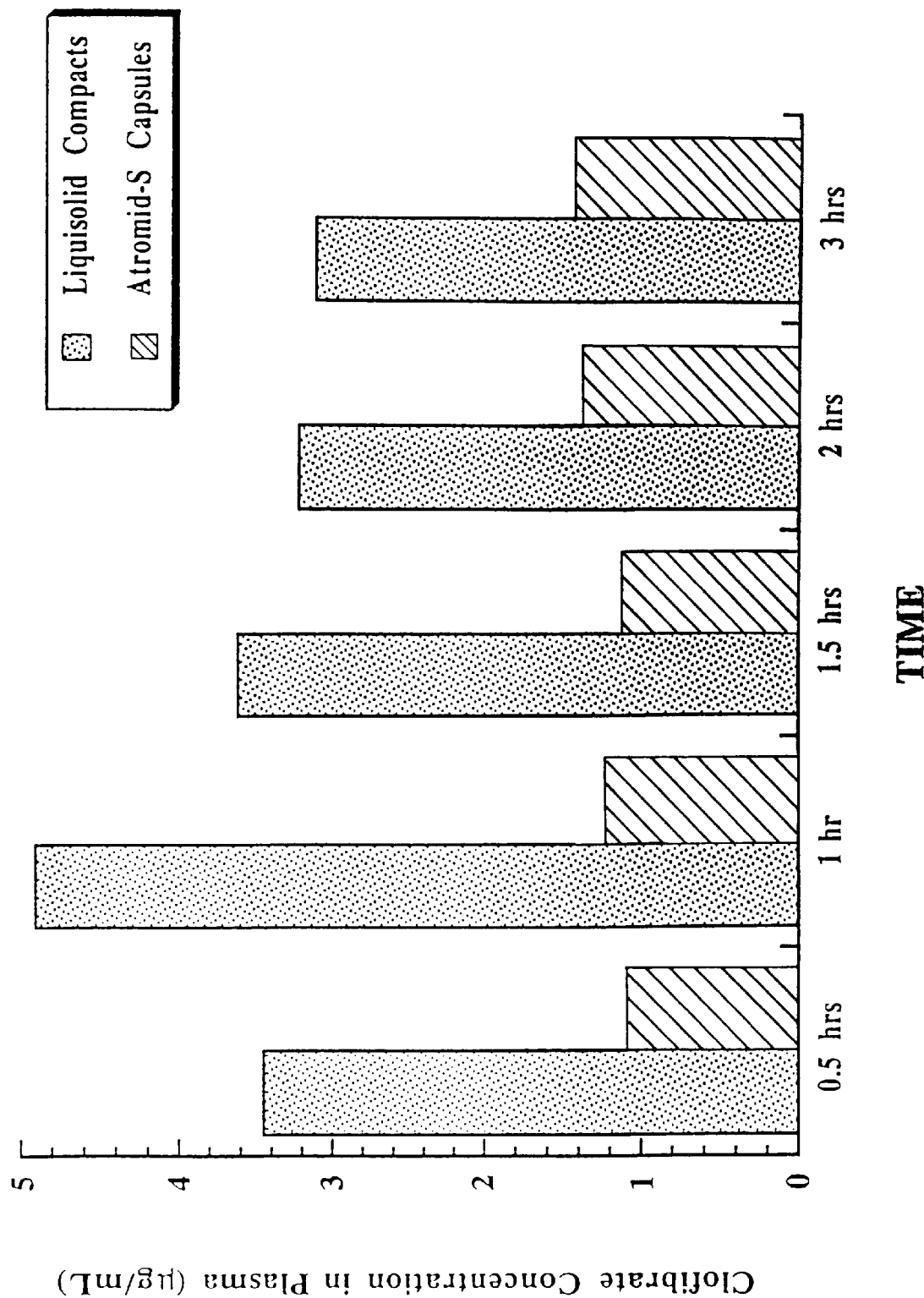
FIG. 6 is a graph showing clofibrate plasma levels in rats over a period of three hours for formulations comprising 10 mg/kg of liquisolid compacts or commercial Atromid-S soft gelatin capsules.

Since drug dissolution is the rate limiting step in oral drug absorption of nonpolar molecules, liquisolid systems might also present a substantial in-vivo superiority over their commercial counterparts. In fact, controlled in-vivo studies using clofibrate liquisolid and commercial products, recently conducted in rats, have confirmed the superior in-vitro release patterns of liquisolid compacts. As shown in FIG. 6, the extent and rate of systemic absorption of this nonpolar molecule from liquisolid tablets were significantly greater than those from the costly commercial soft gelatin capsules. Such findings might even permit the use of lower doses.

Figure 7:
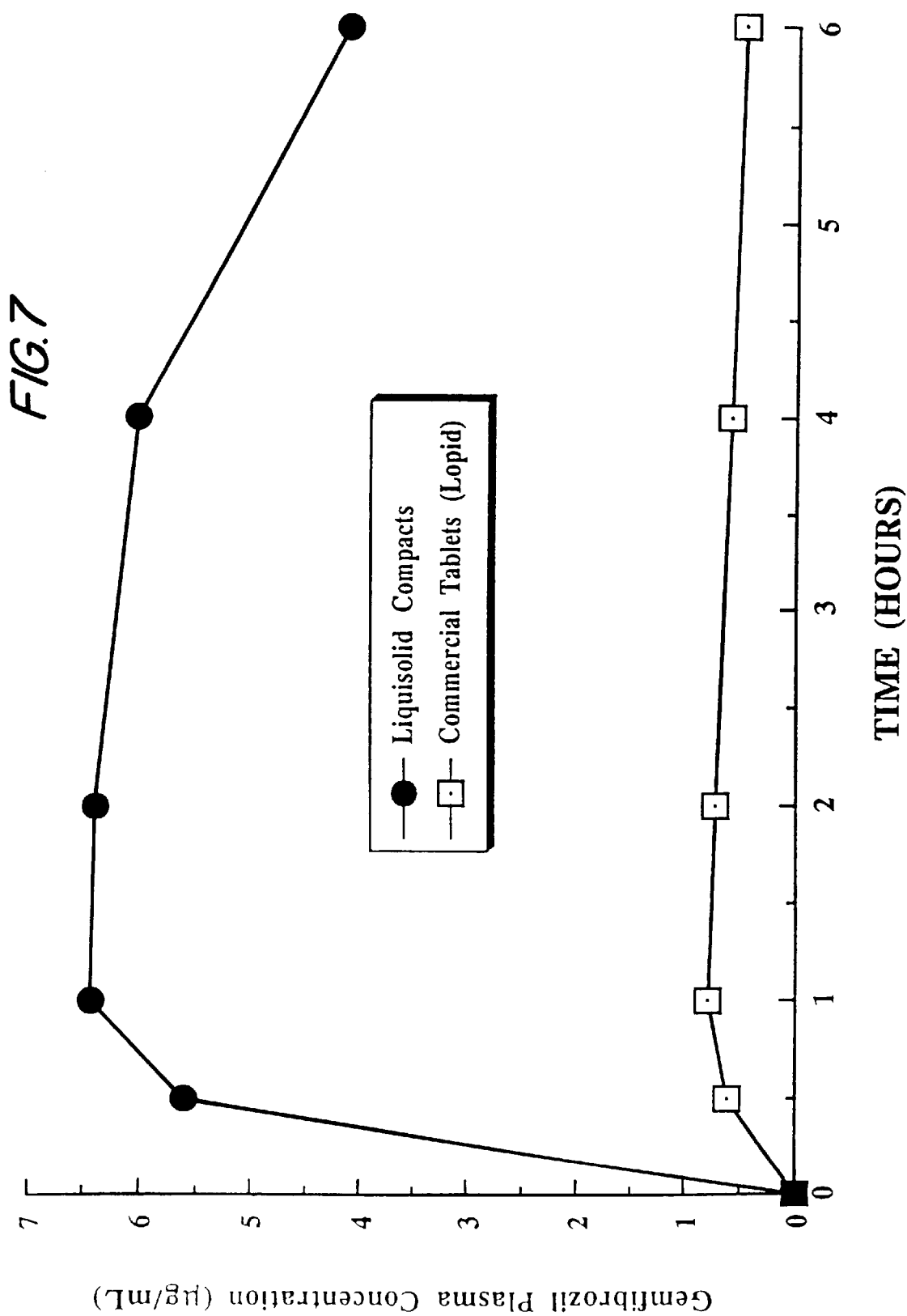
FIG. 7 is a graph showing gemfibrozil plasma levels in rats over a period of six hours after oral administration (10 mg/kg) of a immediate-release liquisolid compact formulation and commercial Lopid 600 mg tablets.
Figure 8:
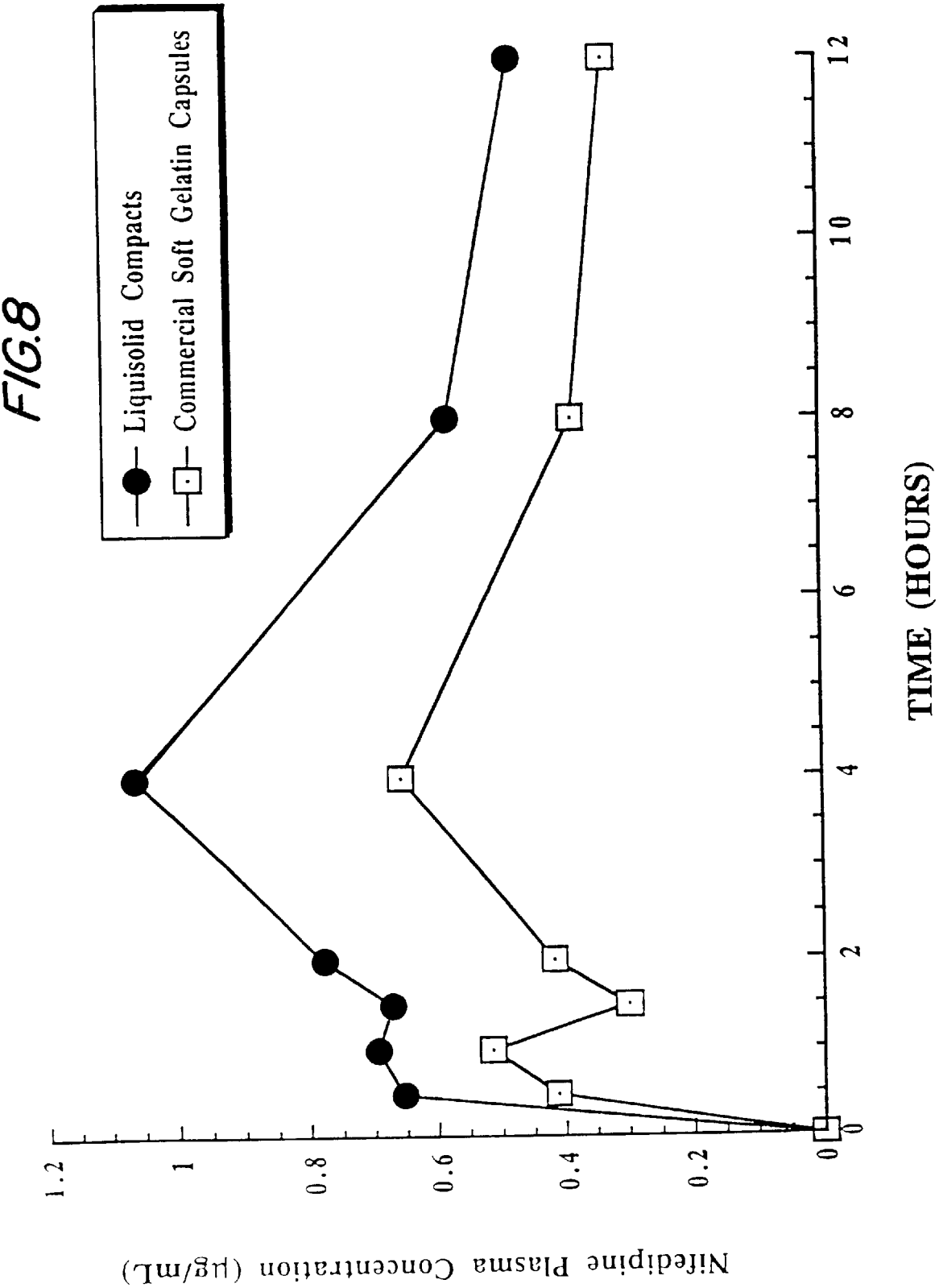
FIG. 8 is a graph showing nifedipine plasma levels in rats over a period of twelve hours after oral administration (0.1 mg/kg) of a immediate release liquisolid compact formulation and commercial soft gelatin capsules.

Furthermore, as shown in FIGS. 7 and 8, liquisolid compacts of gemfibrozil and nifedipine displayed significantly superior drug plasma levels in rats as compared to their highly expensive commercial counterparts. Specifically, a 10 to 12 times higher bioavailability of gemfibrozil in rats was observed from liquisolid compacts (GFZ, 60 mg) as compared to its commercial counterpart (LOPID 600 mg tablets). A three to four times higher bioavailability of nifedipine in rats was observed from liquisolid compacts (NFD-RR, 5 mg) as compared to its commercial counterpart (soft gelatin capsules of nifedipine). Such findings suggest that the bioavailability of gemfibrozil and nifedipine from liquisolid compacts may be significantly enhanced in humans, that lower doses may be possible, and that more economic products could be made.

Figure 5:
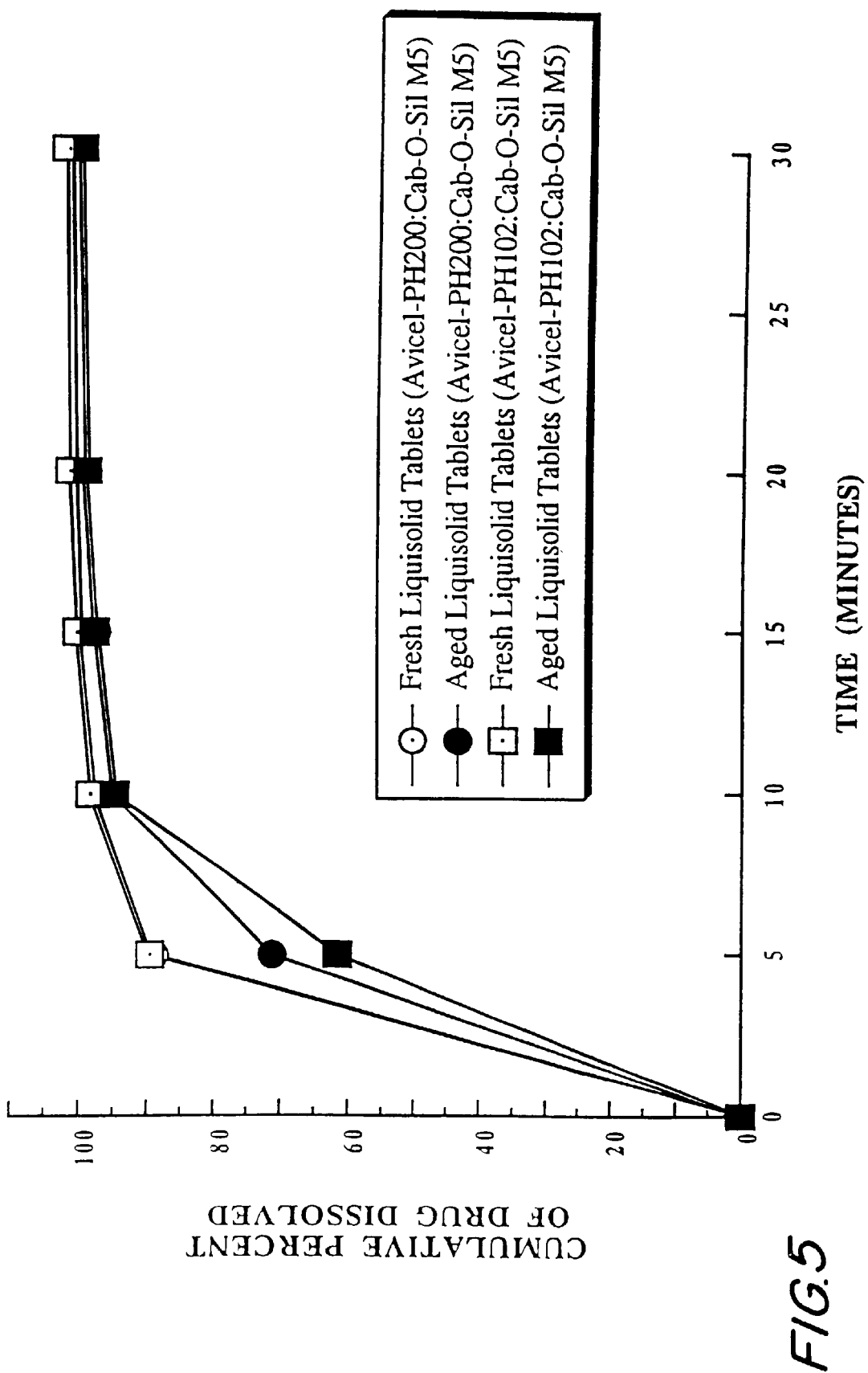
FIG. 5 is a graph showing the comparative dissolution profiles of fresh and 10-months old hydrocortisone liquisolid tablets.

Finally, dissolution profiles and crushing strengths of fresh and 10-months old HSN-3 and HSN-4 liquisolid tablets of hydrocortisone are presented in Table 9. Although it appears that the tablet hardness of the systems deteriorated due to the presence of liquid, the observed decrease in crushing strength is only about 6% to 9% of the original tablet hardness. A comparison of the dissolution curves of fresh and aged hydrocortisone liquisolid tablets is also illustrated in FIG. 5, which shows that, except for the first five minutes, the dissolution rates were not significantly different.

A representative sample for the potential of sustained-release liquisolid compacts is given in FIG. 9. As shown there, the in-vitro release rate of nifedipine (over a 12-hour period) from sustained-release liquisolid tablets was more constant (zero-order release) than that displayed by its highly expensive commercial counterpart (PROCARDIA-XL).

In very recent studies, the effects of various formulation parameters such as excipient ratio, load factor, disintegrant level, solvent system and drug solution concentration on the drug release of liquisolid systems were investigated. It has been shown that these parameters may affect, to various extents, the dissolution characteristics of liquisolid compacts, and thus they may be used for optimization.

The invention is not limited by the embodiments described above which are presented as examples only but can be modified in various ways within the scope of protection defined by the appended patent claims.

REFERENCES

W. R. Ebert. Soft elastic gelatin capsules: unique dosage form. *Pharm. Tech.*, 1:44–50 (1977).

2. E. Nelson. Physicochemical and pharmaceutic properties of drugs that influence the results of clinical trials. *Clin. Pharmacol. Ther.*, 3:673–681 (1962).

3. S. Spireas. *Development of a New Theory for Powdered Solution Technology and Evaluation of Microcrystalline and Amorphous Celluloses as Carriers for Prednisolone Powdered Solutions*. Master of science thesis, St. John's University, Jamaica, N.Y., 1988.

4. S. Spireas, C. I. Jarowski and B. D. Rohera. *Powdered Solution Technology: Principles and Mechanism. Pharm. Res.*, 9:1351–1368 (1992).
5. C. C. Liao. *Physicochemical Properties of Selected Powdered Drug Solutions.* Doctor of philosophy thesis, St. John's University, Jamaica, N.Y., 1983.
6. H. M. Lin. *The Use of Amorphous Silicas as Carriers for a Liquid Drug, Chlorpheniramine Sustained Release Tablets.* Master of science thesis, St. John's University, Jamaica, N.Y., 1986.
7. M. Rahman. *A Physicochemical Study of Tablets Containing Powdered Solutions of Methylene Blue and Spironolactone.* Master of science thesis, St. John's University, Jamaica, N.Y., 1988.
8. A. K. Sheth and C. I. Jarowski. Use of Powdered Solutions to Improve the Dissolution Rate of Polythiazide Tablets. *Drug Dev. Ind. Pharm.*, 16:769–777 (1990).
9. S. Spireas. *Theoretical and Practical Aspects of "Liquisolid Compacts".* Doctoral dissertation, St. John's University, Jamaica, N.Y., 1993 (to be published).
10. *Remington's Pharmaceutical Sciences,* Seventeenth Edition, Mack Publishing Company, Easton, Pa., 1985.
11. *The United States Pharmacopeia XXII,* United States Pharmacopeial Convention, Inc., Rockville, Md., 1990.

What is claimed is:

1. A free-flowing and readily compressible liquid/powder admixture produced by converting a liquid medication into a liquisolid system, comprising the steps of:

(a) selecting a weight (W) of the liquid medication to be included in a single liquisolid system;

(b) selecting a carrier material and a coating material to be included in the liquisolid system;

(c) determining the characteristic minimum carrier:coating ratio, $R_{min}$, and flowable liquid-retention potentials of the carrier ($\Phi$) and coating ($\phi$) materials using a liquisolid flowability test;

(d) determining the characteristic compressible liquid-retention potentials of the carrier ($\Psi$) and coating ($\psi$) materials using a liquisolid compressibility test;

(e) selecting a carrier:coating ratio, R, where $R > R_{min}$, of the carrier and coating materials to be included in the liquisolid system, wherein R=Q/q, Q=the weight of the carrier material, and q=the weight of the coating material;

(f) calculating the optimum liquid load factor ($L_o$) of the system according to the equations:

$$L_o = {}^{\Phi}L_f \text{ when } {}^{\Phi}L_f < {}^{\Psi}L_f$$

or $$L_o = {}^{\Psi}L_f \text{ when } {}^{\Phi}L_f > {}^{\Psi}L_f$$

where:

$${}^{\Phi}L_f = \Phi + \phi(1/R)$$

and $${}^{\Psi}L_f = \Psi + \psi(1/R);$$

(g) calculating the optimum quantities of the carrier ($Q_o$) and coating ($q_o$) materials according to the equations:

$$Q_o = W/L_o$$

$$q_o = Q_o/R$$

(h) admixing the liquid medication with the calculated quantity of carrier material ($Q_o$); and (i) blending the resulting wet mixture with the calculated amount of coating material ($q_o$) to produce a nonadherent, free-flowing and compressible liquid/powder admixture.

2. The liquid/powder admixture of claim 1, further comprising an amount of lubricant effective for tabletting or encapsulating the liquid/powder admixture.

3. The liquid/powder admixture of claim 2, further comprising an amount of disintegrant effective to produce liquisolid compacts possessing immediate drug release properties.

4. The liquid/powder admixture of claim 2, further comprising an amount of binder effective to produce liquisolid compacts possessing sustained drug release properties.

5. The liquid/powder admixture of claim 1, wherein the liquid medication is a drug solution, a drug suspension or a liquid drug.

6. The liquid/powder admixture of claim 5, wherein the drug solution and drug suspension each comprises a solid water-insoluble drug in a solvent and the liquid drug is a liquid lipophilic medication.

7. The liquid/powder admixture of claim 3, wherein the liquisolid compacts are tablets or capsules.

8. The liquid/powder admixture of claim 4, wherein the liquisolid compacts are tablets or capsules.

9. The liquid/powder admixture of claim 1, wherein the carrier material comprises a porous material possessing sufficient absorption properties to permit absorption of the liquid medication into the carrier material.

10. The liquid/powder admixture of claim 9, wherein the carrier material is microcrystalline cellulose or amorphous cellulose.

11. The liquid/powder admixture of claim 1, wherein the coating material comprises a material having a particle size of about 10 nm to 5,000 nm and possessing sufficient adsorptive properties to permit adsorption of the coating material onto the wet mixture, thereby converting the wet mixture into the nonadherent, flowable and compressible liquid/powder admixture.

12. The liquid/powder admixture of claim 11, wherein the coating material is an amorphous silicon dioxide.

13. The liquid/powder admixture of claim 1, wherein the liquisolid flowability test of step (c) comprises:

(a) preparing several powder systems each containing a carrier material and a coating material and selecting for each system a carrier:coating ratio, $R_{1 \ldots x}$, where $_{1 \ldots x}$ corresponds to the powder systems prepared, $R_{1 \ldots x} = Q_{1 \ldots x}/q_{1 \ldots x}$, $Q_{1 \ldots x}$ = the weight of the carrier material, and $q_{1 \ldots x}$ = the weight of the coating material;

(b) preparing several uniform liquid/powder admixtures of different liquid/solid weight compositions ($C_w$) by combining one of the powder systems prepared in step (a) with increasing amounts of the solvent included in the liquid medication of claim 6;

(c) assessing the flow rate and consistency of the admixtures thus obtained using a recording powder flowmeter and determining from this assessment the flowable liquid load factor (${}^{\Phi}L_f$) of the powder system which complies with a pre-selected limit of acceptable flowability, where ${}^{\Phi}L_f = W/Q$, W=the weight of the liquid and Q=the weight of the carrier material;

(d) repeating steps (b) and (c) for the remaining powder systems of step (a) to determine the flowable liquid load factors of these systems; and (e) plotting the flowable liquid load factors ($^{\Phi}L_f$) thus obtained against the corresponding reciprocal carrier:coating ratios (1/R) of the powder systems, thereby obtaining a linear plot having a Y-intercept equal to the flowable liquid-retention potential of the carrier material ($\Phi$) and a slope equal to the flowable liquid-retention potential of the coating material ($\phi$).

14. The liquid/powder admixture of claim 1, wherein the liquisolid compressibility test of step (d) comprises:

(a) preparing several powder systems each containing a carrier material and a coating material and selecting for each system a carrier:coating ratio, $R_{1 \ldots x}$, where $_{1 \ldots x}$ corresponds to the powder systems prepared,
$R_{1 \ldots x} = Q_{1 \ldots x}/q_{1 \ldots x}$,
$Q_{1 \ldots x}$=the weight of the carrier material, and
$q_{1 \ldots x}$=the weight of the coating material;

(b) preparing several uniform liquid/powder admixtures of different liquid/solid weight compositions by combining one of the powder systems prepared in step (a) with increasing amounts of the solvent included in the liquid medication of claim 6;

(c) compressing each liquid/powder admixture thus obtained into tablets using plateau compressional force to achieve maximum tablet crushing strength;

(d) assessing the average tablet crushing strength, $S_c$, of the tablets produced and calculating their pactisity, $\Omega$, where $\Omega = S_c/W_t$ and $W_t$=the average tablet weight in grams;

(e) determining the average liquid content of the crushed tablets and calculating the net liquid/solid weight composition ($C_w$) of the crushed liquid/powder admixture;

(f) determining the characteristic intrinsic pactisity, $\Omega_o$, and sponge index $\sigma_i$, of the powder system by plotting the data obtained as log $\Omega$ versus $C_w$, where log $\Omega$=log $\Omega_o - \sigma_i \cdot C_w$;

(g) determining the $\Psi_{mix}$ of the powder system, where $\Psi_{mix}$=(log $\Omega_o$–log 20)/$\sigma_i$;

(h) determining the compressible liquid-load factor ($^{\Psi}L_f$) of the powder system, where $^{\Psi}L_f = \Psi_{mix}(1+1/R)$;

(i) repeating steps (b) through (h) for the remaining powder systems of step (a) to determine their compressible liquid load factors; and (j) plotting the compressible liquid load factors thus obtained against the corresponding reciprocal carrier:coating ratios (1/R) of the powder systems, thereby obtaining a linear plot having a Y-intercept equal to the compressible liquid-retention potential of the carrier material ($\Psi$) and a slope equal to the compressible liquid-retention potential of the coating material ($\psi$).

15. A free-flowing liquid/powder admixture produced by converting a liquid medication into a liquisolid microsystem, comprising the steps of:

(a) selecting a weight (W) of the liquid medication to be included in a single liquisolid microsystem;

(b) selecting a carrier material and a coating material to be included in the liquisolid microsystem;

(c) determining the characteristic minimum carrier:coating ratio, $R_{min}$, and flowable liquid-retention potentials of the carrier ($\Phi$) and coating ($\phi$) materials using a liquisolid flowability test;

(d) selecting a carrier:coating ratio, R, where $R > R_{min}$, of the carrier and coating materials to be included in the liquisolid micro system, wherein R=Q/q, Q=the weight of the carrier material, and q=the weight of the coating material;

(e) calculating the optimum liquid load factor ($L_o$) of the micro system according to the equations:

$$L_o = {}^{\Phi}L_f \text{ when } {}^{\Phi}L_f < {}^{\Psi}L_f$$

or $$L_o = {}^{\Psi}L_f \text{ when } {}^{\Phi}L_f > {}^{\Psi}L_f$$

where:

$${}^{\Phi}L_f = \Phi + \phi(1/R)$$

and $${}^{\Psi}L_f = \Psi + \psi(1/R);$$

(f) calculating the optimum quantities of the carrier ($Q_o$) and coating ($q_o$) materials according to the equations:

$$Q_o = W/L_o$$

$$q_o = Q_o/R$$

(g) admixing the liquid medication with the calculated quantity of carrier material ($Q_o$); and (h) blending the resulting wet mixture with the calculated amount of coating material ($q_o$) to produce a nonadherent, free-flowing liquid/powder admixture.

16. The liquid/powder admixture of claim 15, further comprising an amount of lubricant effective for encapsulating the liquid/powder admixture.

17. The liquid/powder admixture of claim 16, further comprising an amount of disintegrant effective to produce liquisolid microsystems possessing immediate drug release properties.

18. The liquid/powder admixture of claim 16, further comprising an amount of binder effective to produce liquisolid microsystems possessing sustained drug release properties.

19. The liquid/powder admixture of claim 15, wherein the liquid medication is a drug solution, a drug suspension or a liquid drug in combination with polyvinylpyrrolidone.

20. The liquid/powder admixture of claim 19, wherein the drug solution and drug suspension each comprises a solid water-insoluble drug in solvent and the liquid drug is a liquid lipophilic medication.

21. The liquid/powder admixture of claim 15, wherein the carrier material comprises a porous material possessing sufficient absorption properties to permit absorption of the liquid medication into the carrier material.

22. The liquid/powder admixture of claim 21, wherein the carrier material is microcrystalline cellulose or amorphous cellulose.

23. The liquid/powder admixture of claim 15, wherein the coating material comprises a material having a particle size of about 10 nm to 5,000 nm and possessing sufficient adsorptive properties to permit adsorption of the coating material onto the wet mixture, thereby converting the wet mixture into the nonadherent, flowable and compressible liquid/powder admixture.

24. The liquid/powder admixture of claim 23, wherein the coating material is an amorphous silicon dioxide.

25. The liquid/powder admixture of claim 15, wherein the liquisolid flowability test of step (c) comprises:

(a) preparing several powder systems each containing a carrier material and a coating material and selecting for each system a carrier:coating ratio, $R_{1 \ldots x}$, where $_{1 \ldots x}$ corresponds to the powder systems prepared, $R_{1 \ldots x} = Q_{1 \ldots x}/q_{1 \ldots x}$, $Q_{1 \ldots x}$ = the weight of the carrier material, and $q_{1 \ldots x}$ = the weight of the coating material;

(b) preparing several uniform liquid/powder admixtures of different liquid/solid weight compositions ($C_w$) by combining one of the powder systems prepared in step (a) with increasing amounts of the solvent included in the liquid medication of claim 20;

(c) assessing the flow rate and consistency of the admixtures thus obtained using a recording powder flowmeter and determining from this assessment the flowable liquid load factor ($^\Phi L_f$) of the powder system which complies with a pre-selected limit of acceptable flowability, where $^\Phi L_f = W/Q$, W=the weight of the liquid and Q=the weight of the carrier material;

(d) repeating steps (b) and (c) for the remaining powder systems of step (a) to determine the flowable liquid load factors of these systems; and (e) plotting the flowable liquid load factors ($^\Phi L_f$) thus obtained against the corresponding reciprocal carrier:coating ratios (1/R) of the powder systems, thereby obtaining a linear plot having a Y-intercept equal to the flowable liquid-retention potential of the carrier material ($\Phi$) and a slope equal to the flowable liquid-retention potential of the coating material ($\phi$).

* * * * *